US011858904B2

(12) United States Patent
Schenck et al.

(10) Patent No.: US 11,858,904 B2
(45) Date of Patent: Jan. 2, 2024

(54) PROCESS FOR PREPARING LARGE SIZE ISOXAZOLINE PARTICLES

(71) Applicant: Intervet Inc., Madison, NJ (US)

(72) Inventors: Luke Ryan Schenck, Yardley, PA (US); Athanas Koynov, Metuchen, NJ (US); George X. Zhou, Princeton Junction, NJ (US); Aaron Cote, West Windsor, NJ (US)

(73) Assignee: Intervet Inc., New (JE)

( * ) Notice: Subject to any disclaimer, the term of this patent is extended or adjusted under 35 U.S.C. 154(b) by 450 days.

(21) Appl. No.: 16/761,695

(22) PCT Filed: Nov. 6, 2018

(86) PCT No.: PCT/EP2018/080230
§ 371 (c)(1),
(2) Date: May 5, 2020

(87) PCT Pub. No.: WO2019/091940
PCT Pub. Date: May 16, 2019

(65) Prior Publication Data
US 2020/0331867 A1    Oct. 22, 2020

Related U.S. Application Data

(60) Provisional application No. 62/608,904, filed on Dec. 21, 2017, provisional application No. 62/582,381, filed on Nov. 7, 2017.

(51) Int. Cl.
C07D 261/04    (2006.01)
A01N 43/80    (2006.01)
(52) U.S. Cl.
CPC .......... *C07D 261/04* (2013.01); *A01N 43/80* (2013.01); *C07B 2200/13* (2013.01)
(58) Field of Classification Search
CPC ................................................. C07D 261/04
See application file for complete search history.

(56) References Cited

U.S. PATENT DOCUMENTS

| | | | |
|---|---|---|---|
| 9,609,869 | B2 | 4/2017 | Cassayre et al. |
| 2007/0066617 | A1 | 3/2007 | Mita et al. |
| 2011/0144349 | A1 | 6/2011 | Kousaka et al. |
| 2014/0121194 | A1 | 5/2014 | Ikari |
| 2015/0005507 | A1 | 1/2015 | Matoba et al. |
| 2017/0239218 | A1 | 8/2017 | Le Hir De Fallois et al. |

FOREIGN PATENT DOCUMENTS

| | | |
|---|---|---|
| CN | 102149695 A | 8/2011 |
| CN | 102596172 A | 7/2012 |
| CN | 102858417 A | 1/2013 |
| CN | 102947278 A | 2/2013 |
| CN | 103800324 A | 5/2014 |
| CN | 105813651 A | 7/2016 |
| EP | 2308857 A1 | 4/2011 |
| JP | 2013528177 A | 7/2013 |
| JP | 2014111578 A | 6/2014 |
| JP | 2015028006 A | 2/2015 |
| WO | 2005085216 A1 | 9/2005 |
| WO | 2007079162 A1 | 7/2007 |
| WO | 2009002809 A2 | 12/2008 |
| WO | 2009003075 A1 | 12/2008 |
| WO | 2009024541 A2 | 2/2009 |
| WO | 2010005048 A1 | 1/2010 |
| WO | 2010070068 A2 | 6/2010 |
| WO | 2010079077 A1 | 7/2010 |
| WO | 2010149727 A2 | 12/2010 |
| WO | 2011149749 A1 | 12/2011 |
| WO | 2014126208 A1 | 8/2014 |
| WO | 2015048371 A1 | 4/2015 |
| WO | 2015091898 A1 | 6/2015 |
| WO | 2016138339 A1 | 9/2016 |
| WO | 2016164487 A1 | 10/2016 |
| WO | 2019091936 A1 | 5/2019 |

OTHER PUBLICATIONS

Intervet, Inc., Corrected Freedom of Informatioan Summary, NADA 141-426, 2014, 1-40, N/A.
Kilp, S et al., Pharmacokinetics of fluralaner in dogs following a single oral or intravenous administration, Parasites & Vectors, 2014, 1-5, 7:85.
Knunyants, I.L. (Editor), Chemical Encyclopedic Dictionary, Moscow, Soviet Encyclopaedia, 1983, 130-131, N/A.
Knunyants, I.L. (Editor), Khimicheskii Entsiklopedicheskii Slovar, Moscow, Sovetskaya Entsiklopediya, 1983, 130-131, N/A.
Laguerie, C. et al., Crystallization and Crystallizing Processes to Produce Controlled-Properties Solid Particles, KONA Powder and Particle Journal, 1994, 17-26, 12.
Guranda, D.F. et al., Synthesis methods and drug production technology. Obtaining polymorphic modifications of medicinal substances, Chemical Pharmaceutical Journal, 2010, 1-7 (Translated from Khimiko-Farmatsevticheskii Zhurnal, vol. 44, No. 5, pp. 22-28, May 2010), 44(5).

*Primary Examiner* — Shawquia Jackson
(74) *Attorney, Agent, or Firm* — David J. Kerwick

(57) ABSTRACT

The application relates to a process to produce large isoxazoline compound particles which comprises initiating crystallization and then maintaining the temperature of the crystallization in the metastable region by removing, reheating and recycling a portion of the solvent thereby allowing the existing crystals to grow larger while minimizing the formation of newer smaller crystals.

4 Claims, 17 Drawing Sheets

SEM of the material generated from the unseeded, distallative crystallization process from the commercial EtOAc:Toluene process.

FIG. 5

Pressure titration of fluralaner crystals not produced by the inventive process

| Project | Mv μm | x(10%) μm | x(50%) μm | x(90%) μm | x(95%) μm | xstdd.(3) μm |
|---|---|---|---|---|---|---|
| Run 15 Final | 121.66 | 19.41 | 111.94 | 227.65 | 281.07 | 85.75 |
| Run 15 Final | 113.03 | 18.70 | 107.10 | 211.42 | 244.99 | 73.71 |
| Run 15 Final | 118.06 | 18.59 | 109.90 | 223.23 | 268.14 | 81.23 |
| Run 15 Final | 96.64 | 10.90 | 81.20 | 193.84 | 247.01 | 83.13 |
| Run 15 Final | 91.00 | 10.59 | 78.59 | 184.64 | 226.92 | 72.66 |
| Run 15 Final | 76.06 | 7.64 | 58.83 | 166.84 | 205.63 | 68.39 |
| Run 15 Final | 89.83 | 8.02 | 62.78 | 188.47 | 286.14 | 99.42 |
| Run 15 Final | 70.32 | 7.57 | 57.35 | 154.06 | 181.08 | 57.27 |

SEM image of fluralaner crystals produced by a process that is not the inventive process.

Bravecto  2018/01/08  13:33 NL  D5.3  x300  300 μm

SEM of material made from non optimized recirculation process, where it can be seen that the particles are thinner than those from the optimized process and are not mechanically resilient. Note that this is an SEM of the particles.

SEM image of fluralaner crystals produced by the inventive process.

SEM of the material made from Example 3.
Resulting material had an d50 of 108, and an approximately 24% reduction in d50 from the pressure titration from 1bar to 3bar.

Bravecto  2018/02/09  11:58 NL  D6.2  x1.0k  100 μm

Schematic of the pilot scale equipment and process used to generate the material outlined in Example 4.

SEM of the material made from Example 4.

SEM of the material made from Example 5, showing morphological differences resulting from the different solvent system.

PROCESS FOR PREPARING LARGE SIZE ISOXAZOLINE PARTICLES

CROSS-REFERENCE TO RELATED APPLICATIONS

This application is a national stage entry under 35 U.S.C. § 371 of PCT/EP2018/080230 filed on Nov. 6, 2018, which claims priority under 35 U.S.C. § 119(e) of provisional application U.S. Ser. No. 62/582,381 filed Nov. 7, 2017, and U.S. Ser. No. 62/608,904 filed on Dec. 21, 2017, the contents of which are hereby incorporated by reference in their entireties.

BACKGROUND

Isoxazoline compounds are known in the art and these compounds and their use as antiparasitic are described, for example, in US patent application US 2007/0066617, and International Patent applications WO 2005/085216, WO 2007/079162, WO 2009/002809, WO 2009/024541, WO 2009/003075, WO 2010/070068 and WO 2010/079077, the disclosures of which, as well as the references cited herein, are incorporated by reference. This class of compounds is known to possess excellent activity against ectoparasites, i.e. parasitic insect and acarids, such as fleas and ticks and endoparasites such as nematodes.

Examples of isoxazoline compounds are carbamoyl benzamide phenyl isoxazoline (CBPI) compounds. A specific example of a CBPI compound is 4-[5-(3,5-Dichlorophenyl)-5-trifluoromethyl-4,5-dihydroisoxazol-3-yl]-2-methyl-N-[(2,2,2-trifluoro-ethylcarbamoyl)-methyl]-benzamide (CAS RN [864731-61-3])—USAN fluralaner.

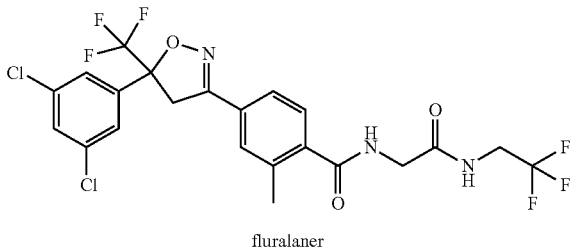 [SMILES: Cc1cc(C2=NOC(c3cc(Cl)cc(Cl)c3)(C(F)(F)F)C2)ccc1C(=O)NCC(=O)NCC(F)(F)F]

fluralaner

The CBPI compound fluralaner is disclosed in patent application WO 2005/085216.

Bravecto® is a chewable tablet which contains fluralaner approved for the treatment and prevention of flea infestations and the treatment and control of tick infestations in dogs (see NADA 141-426, May 15, 2014).

Crystallization is a commonly used technique for the purification of chemical and pharmaceutical substances. It is a separation technique in which solids are separated from a solution. When a solid substance (solute) is mixed with a liquid solvent and stirred, the solute dissolves in the solvent to form a solution. As more and more solute is added to the solvent, a point comes after which no more solute can be dissolved in the solvent. This point is known as the saturation point, and the solution is called a saturated solution. For most substances, the amount of solute that can dissolve in the solvent is a function of temperature. As the temperature of the solvent is increased, the amount of solute that can be dissolved increases. When the heated saturated solution is cooled, some of the dissolved solute comes out of the solution and crystals of solute start to form. The size of crystals formed during this process depends on the cooling rate. If the solution is cooled at a fast rate then, it forms tiny crystals in large numbers. Large crystals are formed at slow cooling rates. (see "Crystallization: Separation of Substances" Oct. 31, 2017, https://byjus.com/chemistry/crystallization/accessed Dec. 19, 2017).

A theoretical explanation of the temperature dependence of the formation of crystals is provided below and illustrated in FIG. 1:

"Suppose we start at point A in the diagram, which is under saturated. Any crystals added to a solution in this region would dissolve. If we now cool to a point between A and B, we enter the meta-stable region where existing crystals will grow, but no new crystals are formed. Cooling further we obtain a labile solution at point B where spontaneous formation of new crystals, i.e. nucleation, takes place. This dramatically decreases the concentration and point C will be reached. Cooling further, the crystals formed between B and C grow and consume whatever supersaturation we create by cooling, so we stay in the meta stable region until we reach the end of the crystallization at point D."

Source: "Practica in Process Engineering II Crystallization" Spring 2014 https://www.ethz.ch/content/dam/ethz/special-interest/mavt/process-engineering/separation-processes-laboratory-dam/documents/practice%20in%20process%20engineering%202/crystallization.pdf, accessed Dec. 19, 2017.

There is no disclosure in any of these references of a process to control the particle size of isoxazoline compound crystals.

SUMMARY OF THE INVENTION

A process for preparing isoxazoline compound particles wherein the isoxazoline compound is a compound of Formula (I)

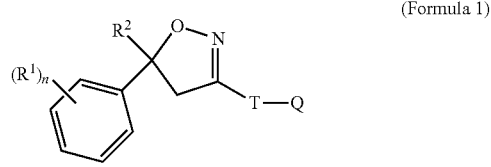

(Formula 1)

wherein
$R^1$=halogen, $CF_3$, $OCF_3$, or CN;
n=integer from 0 up to and including 3;
m=1 or 2;
$R^2$=$C_1$-$C_3$ haloalkyl;
T=ring structure: 5-, or 6-membered, or bicyclic, which is optionally substituted by one or more radicals Y;
Y=methyl, halomethyl, halogen, CN, $NO_2$, $NH_2$—C=S, or two adjacent radicals Y together form a chain;
Q=X—$NR^3R^4$, $NR^5$—$NR^6$—X—$R^3$, X—$R^3$, or a 5-membered N-heteroaryl ring, which is optionally substituted by one or more radicals;
X=$CH_2$, $CH(CH_3)$, CH(CN), CO, CS;
$R^3$=hydrogen, methyl, haloethyl, halopropyl, halobutyl, methoxymethyl, methoxyethyl, halomethoxymethyl, ethoxymethyl, haloethoxymethyl, propoxymethyl, ethylaminocarbonylmethyl, ethylaminocarbonylethyl, dimethoxyethyl, propynylaminocarbonylmethyl, N-phenyl-N-methyl-amino, haloethylaminocarbonyl-methyl, haloethylaminocarbonylethyl, tetrahydrofuryl, methylaminocarbonylmethyl, (N,N-dimethylamino)-carbonylmethyl, propylaminocarbonylmethyl, cyclopropylaminocarbonylmethyl, propenylaminocarbonylmethyl, haloethylaminocarbonylcyclopropyl, alkylsulfanylalkyl, alkylsulfinylalkyl, alkylsulfonylalkyl, cycloalkyl,

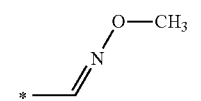
R³-1

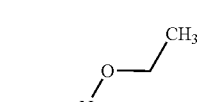
R³-2

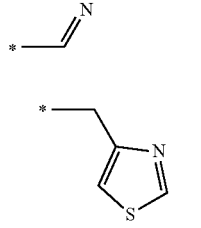
R³-3

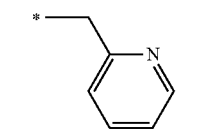
R³-4

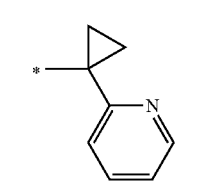
R³-5

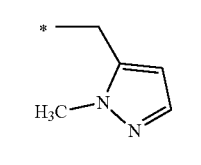
R³-6

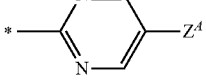
R³-7

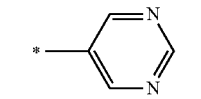
R³-8

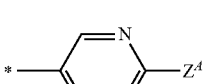
R³-9

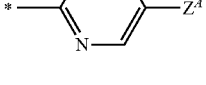
R³-10

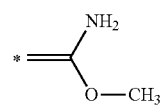
R³-11

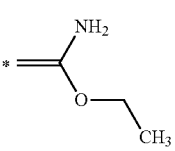
R³-12

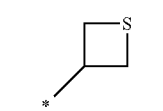
R³-13

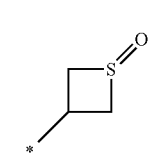
R³-14

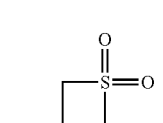
R³-15

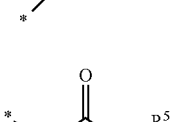
R³-16

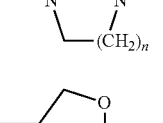
R³-17 or

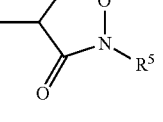
R³-18;

wherein $Z^A$=hydrogen, halogen, cyano, or halomethyl ($CF_3$);

$R^4$=hydrogen, ethyl, methoxymethyl, halomethoxymethyl, ethoxymethyl, haloethoxymethyl, propoxymethyl, methylcarbonyl, ethylcarbonyl, propylcarbonyl, cyclopropylcarbonyl, methoxycarbonyl, methoxymethylcarbonyl, aminocarbonyl, ethylaminocarbonylmethyl, ethylaminocarbonylethyl, dimethoxyethyl, propynylaminocarbonylmethyl, haloethylaminocarbonylmethyl, cyanomethylaminocarbonylmethyl, or haloethylaminocarbonylethyl;

$R^5$=H, alkyl, or haloalkyl;

$R^6$=H, alkyl, or haloalkyl;

or wherein $R^3$ and $R^4$ together form a substituent selected from the group consisting of:

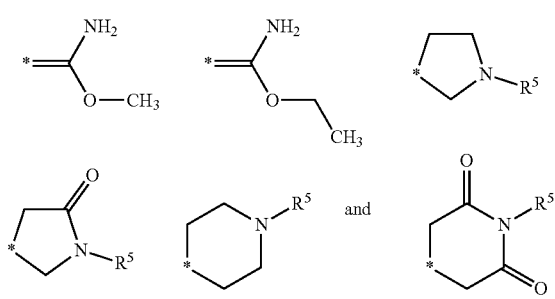

or salt or solvate thereof, comprising
a) Dissolving an isoxazoline compound in a crystallizer vessel with a solvent which has a temperature dependent solubility of the isoxazoline compound to create a batch of isoxazoline compound solution;
b) Initiate crystallization by
  i) cooling the crystallizer vessel to supersaturation or
  ii) vibrating the crystallizer vessel or
  iii) adding crystalline seed of the isoxazoline compound to the crystallizer vessel or
  iv) a combination of one or more of the above;
c) Removing a portion of the batch, heating the removed portion to fully dissolve the isoxazoline compound particles in the solvent and returning the dissolved isoxazoline compound solution to the crystallizer vessel; wherein the rate of return is equal to the rate of removal and is approximately 0.25 to 0.75 batch volumes per hour; and wherein the batch volume is the volume of the isoxazoline compound solution created in step a); and
d) Cooling the crystallizer vessel to achieve isoxazoline compound particles of the desired dimensions;
wherein the desired particle dimensions are particles having a volume weighted particle size distribution (d50) as measured by a light scattering instrument of between 75 and 120 μm and an average particle thickness as measured by scanning electron microscopy of greater than 10 μm, preferably greater than 20 μm.

An isoxazoline compound particle composition comprising particles with a thickness of greater than 10 μm, preferably greater than 20 μm as measured by scanning electron microscopy (SEM), and a mechanical resiliency as measured by a pressure titration using the Sympatec HELOS, wherein the particle size distribution (d50) of the particles does not decrease by more than 40% from 1 to 3 bar dispersion pressure.

DESCRIPTION OF THE FIGURES

FIG. 5—Pressure titration of fluralaner crystals not produced by the inventive process. Sympatec Pressure Titration: as pressure increased from 1-3 bar, particle size (d50) decreases from 50 μm to 25 μm. Material made from non optimized recirculation process. In this case, the crystals are thin, and not mechanically robust, as can be seen from the pressure titration experiment where between 1 bar dispersing pressure and 3 bar dispersing pressure, the ×50 is reduced from 110 um at 1 bar, to 80 um at 2 bar to 60 at 3 bar, or 46% reduction in size from 1 bar to 3 bar.

DETAILED DESCRIPTION

Figure 1:
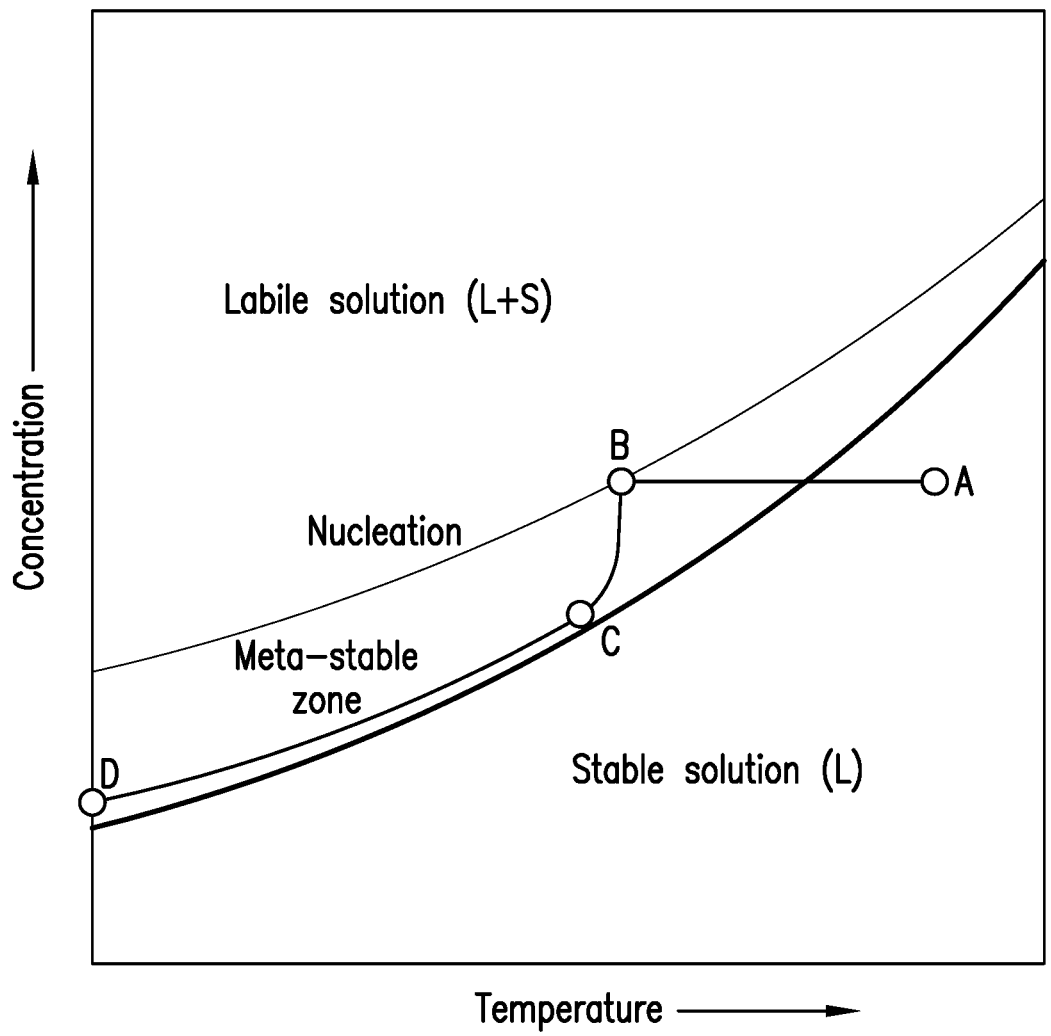
FIG. 1—Temperature dependence of crystal formulation
FIG. 2—Temperature dependence of the solubility of fluralaner in isopropanol (IPA).
Figure 2:
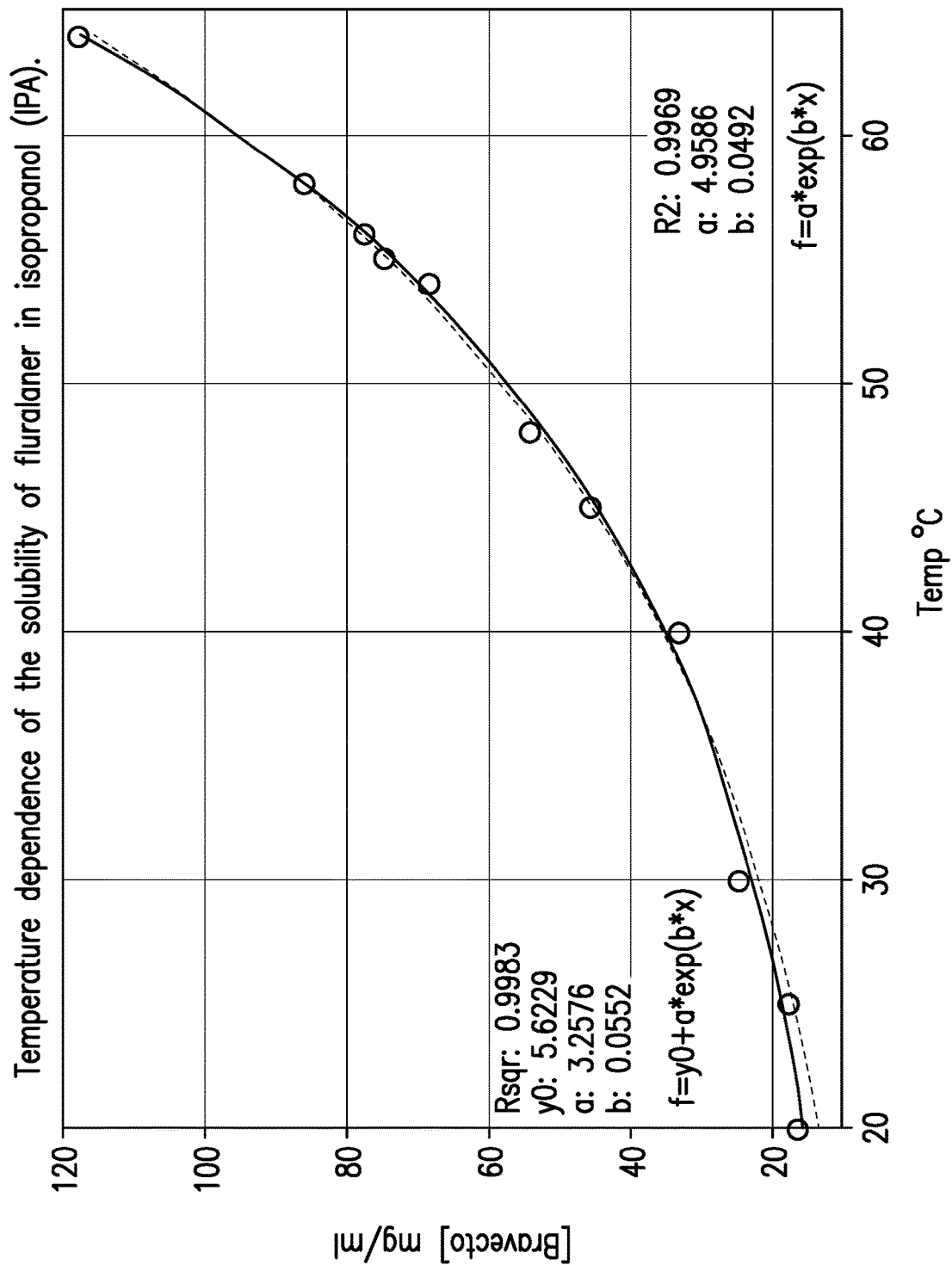

An improved process to produce large isoxazoline compound particles which comprises initiating crystallization and then maintaining the temperature of the crystallization in the metastable region by removing, reheating and recycling a portion of the solvent thereby allowing the existing crystals to grow larger while minimizing the formation of newer smaller crystals.

Crystallization is initiated by nucleation, which happens either spontaneously or is induced by vibration or seed particles. Nucleated crystals are small crystals formed when there is a drop in the temperature of a saturated solution. If nucleation sets in too quickly, too many too small crystals will grow.

In the case of isoxazoline compounds and fluralaner in particular, the seed crystals are typically less than 10 μm length.

The process of crystallization starts with the addition of nucleated material (seed crystals) to a solution of isoxazoline compound in solution to achieve surface properties of the starting crystals that are amenable to growth. As crystallization is initiated, a slurry of isoxazoline compound particles in the solvent is formed. This initial slurry is kept at a relatively high temperature (52-54° C.) to facilitate reasonable growth rates and avoid further nucleation. At lower temperatures, growth rates are significantly slower, and the risk of nucleation is greater. A portion of the batch of isoxazoline compound particle slurry is removed, heated to dissolve any crystals that have formed and returned to the crystallizer to provide continuous supersaturation to drive crystal growth. This recycle rate cannot be too low slow since under these growth conditions thin plates are preferentially formed, which are susceptible to breakage. The recycle rate cannot be too high, since under these conditions either nucleation, or aggregation can occur. Once the starting slurry has grown to a sufficient point, the slurry is cooled at a rate that avoids nucleation to a temperature where the desired crystal dimensions are achieved.

The return of the dissolved isoxazoline compound solution to the crystallizer vessel is conducted at rate of approximately 0.25 to 0.75 batch volumes per hour to achieve continuous crystal growth of the isoxazoline compound particles.

After sufficient particle size growth is achieved from the repeated removal of slurry material from and return of dissolved isoxazoline to the crystallizer, the crystallizer is cooled to about 0° C., preferable about −10° C. over 10-48 hours, preferably 12-20 hours to further relieve supersaturation and achieve growth to the desired dimensions.

It has been found that injectable compositions comprising particles of isoxazoline compounds with a defined particle size produced by the inventive process show desirable bioavailability and duration of efficacy, while causing minimal irritation at the injection site. Such compositions also provide desirable safety profiles toward the warm-blooded and bird animal recipients. In addition, it has been discovered that a single administration of such compositions generally provides potent activity against one or more parasites (e.g., ectoparasites, e.g. fleas, ticks or mites), while also tending to provide fast onset of activity, long duration of activity, and/or desirable safety profiles.

Definitions

Scanning electron microscopy (SEM) is an analytical instrument that uses a focused beam of high-energy electrons to generate a variety of signals at the surface of solid specimens. The signals reveal information about the sample including external morphology (texture), chemical composition, and crystalline structure and orientation of materials making up the sample.

Solvent with temperature dependent solubility for the solute means that the solubility of the solute in the solvent varies with temperature. Generally, this means the solubility increases with increased temperature.

Temperature sensitivity of fluralaner solubility in isopropanol (IPA) is shown in FIG. 1 with the x-axis showing temperature and the y-axis showing the solubility of fluralaner in expressed in mg/mL.

The meta-stable region of the solubility temperature curve is the region where existing crystals will grow, but no new crystals are formed.

Crystallizer vessel is a vessel in which crystallization occurs.

Saturation is the state of a solution when it holds the maximum equilibrium quantity of dissolved matter at a given temperature.

Supersaturation is when a solution contains more solute than the saturated solution at equilibrium.

Slurry is a thin suspension.

Batch is the solvent plus solute.

Batch volume is the volume of the batch.

As used herein, particle size data reported are volume weighted as measured by conventional particle techniques well known to those skilled in the art, such as static light scattering (also known as laser diffraction), image analysis or sieving. More discussion of particle size measurement is provided below.

Mechanical resiliency is the resistance of crystals or particles to break into smaller crystals or particles when exposed to pressure or stress from other sources. Mechanical resiliency can be measured by a pressure titration using the Sympatec HELOS. This instrument can simultaneously measure the particle size distribution. In this experiment, pressure is applied to the crystals to disperse or separate them one from another. The change in the particle size distribution measurement of d50 is monitored as the pressure on the crystals is increased from 1 bar to 3 bars. Preferably, the isoxazoline compound particles of the subject invention will not decrease their particle size distribution measurement of d50 by more than 30-40% when the dispersion pressure is increased from 1 to 3 bar.

In an embodiment of an isoxazoline for use in the invention, T is selected from

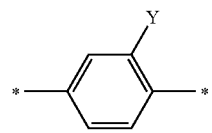

T-1

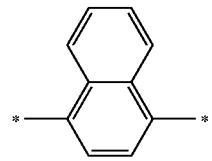

T-2

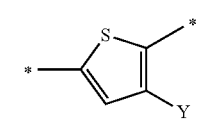

T-3

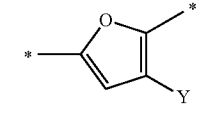

T-4

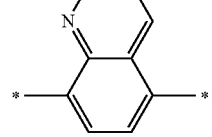

T-5

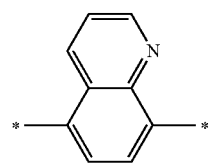

T-6

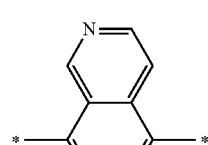

T-7

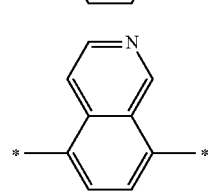

T-8

T-9 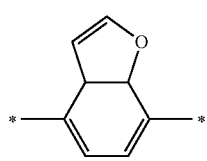
T-10 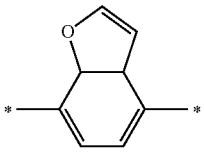
T-11 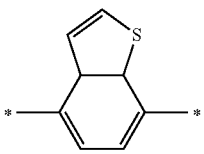
T-12 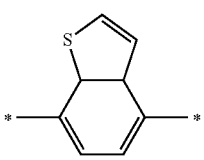
T-13 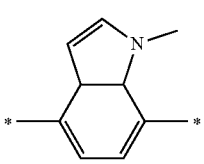
T-14 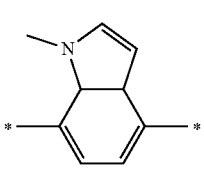
T-15 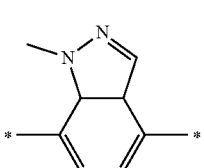
T-16 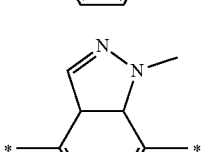
T-17 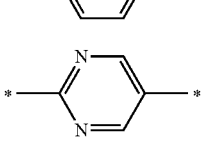
T-18 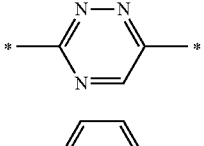
T-19 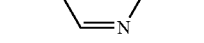
T-20 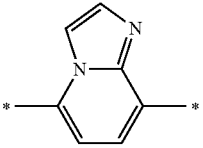
T-21 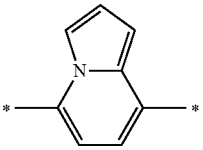
T-22 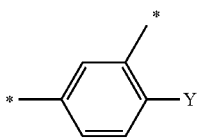
T-23 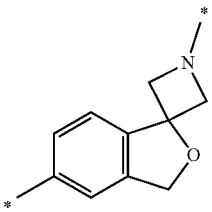
T-24 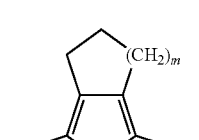
T-25 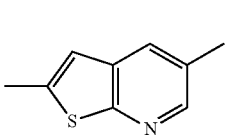
wherein in T-1, T-3 and T-4, the radical Y=hydrogen, halogen, methyl, halomethyl, ethyl, or haloethyl.
In an embodiment of an isoxazoline for use in the invention, Q is selected from
Q-1 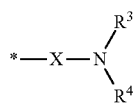
Q-2 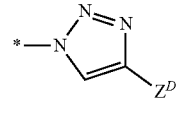
Q-3 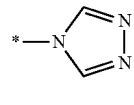
Q-4 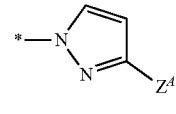

-continued
Q-5
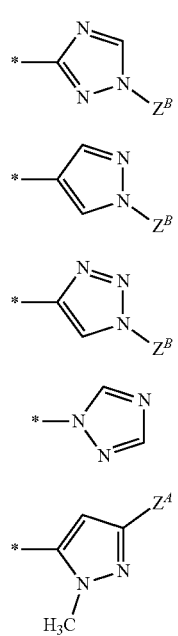
Q-6
Q-7
Q-8
Q-9
wherein R³, R⁴, X and $Z^A$ are as defined above, and
$Z^B=$
$Z^B$-1
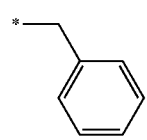
$Z^B$-2
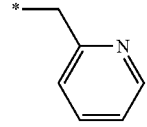
$Z^B$-3
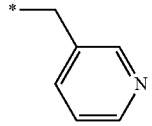
$Z^B$-4
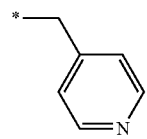
$Z^B$-5
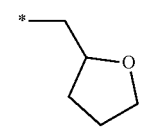
$Z^B$-6
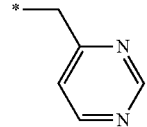
-continued
$Z^B$-7
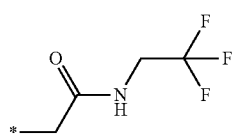
$Z^B$-8
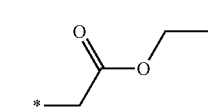
$Z^B$-9
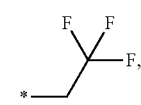
$Z^D=$
$Z^D$-1
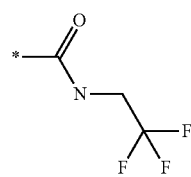
$Z^D$-2
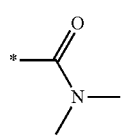
$Z^D$-3
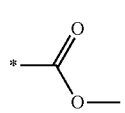
$Z^D$-4
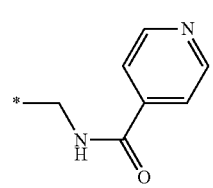
$Z^D$-5
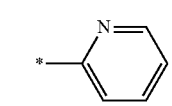
$Z^D$-6
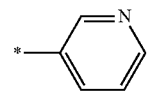

In an embodiment an isoxazoline for use in the invention is as presented in Table 1.

TABLE 1

| $(R^1)_n$ | $R^2$ | $R^3$ | $R^4$ | T | Y | Q | Z | X |
|---|---|---|---|---|---|---|---|---|
| 3-Cl, 5-Cl | $CF_3$ | $CH_2CF_3$ | H | T-2 | — | Q-1 | — | CO |
| 3-Cl, 5-Cl | $CF_3$ | $CH_2CH_3$ | H | T-2 | — | Q-1 | — | CO |
| 3-Cl, 5-Cl | $CF_3$ | $CH_2CH_2OCH_3$ | H | T-2 | — | Q-1 | — | CO |
| 3-Cl, 5-Cl | $CF_3$ | $CH_2C(O)NHCH_2CF_3$ | H | T-2 | — | Q-1 | — | CO |
| 3-Cl, 5-Cl | $CF_3$ | $CH_2C(O)NHCH_2CH_3$ | H | T-2 | — | Q-1 | — | CO |
| 3-$CF_3$, 5-$CF_3$ | $CF_3$ | $CH_2C(O)NHCH_2CF_3$ | H | T-2 | — | Q-1 | — | CO |
| 3-$CF_3$, 5-$CF_3$ | $CF_3$ | $CH_2C(O)NHCH_2CH_3$ | H | T-2 | — | Q-1 | — | CO |
| 3-$CF_3$, 5-Cl | $CF_3$ | $CH_2C(O)NHCH_2CF_3$ | H | T-2 | — | Q-1 | — | CO |
| 3-$CF_3$, 5-Cl | $CF_3$ | $CH_2C(O)NHCH_2CH_3$ | H | T-2 | — | Q-1 | — | CO |
| 3-Cl, 5-Cl | $CF_3$ | — | | T-2 | — | Q-6 | $Z^B$-7 | CO |
| 3-Cl, 5-Cl | $CF_3$ | — | — | T-2 | — | Q-7 | $Z^B$-7 | CO |
| 3-Cl, 5-Cl | $CF_3$ | — | — | T-2 | — | Q-5 | $Z^B$-7 | CO |
| 3-Cl, 5-Cl | $CF_3$ | — | — | T-2 | — | Q-2 | $Z^D$-1 | CO |
| 3-Cl, 5-Cl | $CF_3$ | $CH_2C(O)NHCH_2CF_3$ | H | T-3 | $CH_3$ | Q-1 | — | CO |
| 3-Cl, 5-Cl | $CF_3$ | $CH_2C(O)NHCH_2CC$ | H | T-3 | $CH_3$ | Q-1 | — | CO |
| 3-Cl, 5-Cl | $CF_3$ | $CH_2C(O)NHCH_2CN$ | H | T-3 | $CH_3$ | Q-1 | — | CO |
| 3-Cl, 5-Cl | $CF_3$ | $CH_2C(O)NHCH_2CH_3$ | H | T-3 | $CH_3$ | Q-1 | — | CO |
| 3-$CF_3$, 5-$CF_3$ | $CF_3$ | $CH_2C(O)NHCH_2CF_3$ | H | T-3 | $CH_3$ | Q-1 | — | CO |
| 3-$CF_3$, 5-$CF_3$ | $CF_3$ | $CH_2C(O)NHCH_2CH_3$ | H | T-3 | $CH_3$ | Q-1 | — | CO |
| 3-Cl, 4-Cl, 5-Cl | $CF_3$ | $CH_2C(O)NHCH_2CF_3$ | H | T-3 | $CH_3$ | Q-1 | — | CO |
| 3-Cl, 4-Cl, 5-Cl | $CF_3$ | $CH_2C(O)NHCH_2CH_3$ | H | T-3 | $CH_3$ | Q-1 | — | CO |
| 3-Cl, 4-F, 5-Cl | $CF_3$ | $CH_2C(O)NHCH_2CF_3$ | H | T-3 | $CH_3$ | Q-1 | — | CO |
| 3-Cl, 4-F, 5-Cl | $CF_3$ | $CH_2C(O)NHCH_2CH_3$ | H | T-3 | $CH_3$ | Q-1 | — | CO |
| 3-Cl, 5-Cl | $CF_3$ | $CH_2C(O)NHCH_2CF_3$ | H | T-20 | — | Q-1 | — | CO |
| 3-Cl, 5-Cl | $CF_3$ | $CH_2C(O)NHCH_2CH_3$ | H | T-20 | — | Q-1 | — | CO |
| 3-$CF_3$, 5-$CF_3$ | $CF_3$ | $CH_2C(O)NHCH_2CF_3$ | $CH_3$ | T-20 | — | Q-1 | — | CO |
| 3-$CF_3$, 5-$CF_3$ | $CF_3$ | $CH_2C(O)NHCH_2CH_3$ | $CH_3$ | T-20 | — | Q-1 | — | CO |
| 3-$CF_3$, 5-$CF_3$ | $CF_3$ | $CH_2C(O)NHCH_2CF_3$ | H | T-20 | — | Q-1 | — | CO |
| 3-$CF_3$, 5-$CF_3$ | $CF_3$ | $CH_2C(O)NHCH_2CH_3$ | H | T-20 | — | Q-1 | — | CO |
| 3-$CF_3$, 5-$CF_3$ | $CF_3$ | $CH_2C(O)NHCH_2CF_3$ | H | T-21 | — | Q-1 | — | CO |
| 3-$CF_3$, 5-$CF_3$ | $CF_3$ | $CH_2C(O)NHCH_2CH_3$ | H | T-21 | — | Q-1 | — | CO |
| 3-Cl, 5-Cl | $CF_3$ | $CH_2C(O)NHCH_2CF_3$ | H | T-21 | — | Q-1 | — | CO |
| 3-Cl, 5-Cl | $CF_3$ | $CH_2C(O)NHCH_2CH_3$ | H | T-21 | — | Q-1 | — | CO |
| 3-Cl, 5-Cl | $CF_3$ | $CH_2CH_2SCH_3$ | H | T-21 | — | Q-1 | — | CO |
| 3-Cl, 4-Cl, 5-Cl | $CF_3$ | $C(O)CH_3$ | H | T-22 | F | Q-1 | — | $CH_2$ |
| 3-Cl, 4-Cl, 5-Cl | $CF_3$ | $C(O)CH(CH_3)_2$ | H | T-22 | F | Q-1 | — | $CH_2$ |
| 3-Cl, 4-Cl, 5-Cl | $CF_3$ | $C(O)$-cyclo-propyl | H | T-22 | F | Q-1 | — | $CH_2$ |
| 3-Cl, 4-F, 5-Cl | $CF_3$ | $C(O)CH_3$ | H | T-22 | F | Q-1 | — | $CH_2$ |
| 3-Cl, 4-Cl, 5-Cl | $CF_3$ | $C(O)CH_2CH_3$ | H | T-22 | F | Q-1 | — | $CH_2$ |
| 3-Cl, 4-F, 5-Cl | $CF_3$ | $C(O)CH_3$ | H | T-22 | Cl | Q-1 | — | $CH_2$ |
| 3-Cl, 5-Cl | $CF_3$ | $CH_2C(O)NHCH_2CF_3$ | H | T-1 | $CH_3$ | Q-1 | — | CO |
| 3-Cl, 5-Cl | $CF_3$ | $CH_2C(O)NHCH_2CH_3$ | H | T-1 | $CH_3$ | Q-1 | — | CO |
| 3-Cl, 5-Cl | $CF_3$ | $R^3$-1 (Z) | H | T-1 | $CH_3$ | Q-1 | — | CO |
| 3-Cl, 5-Cl | $CF_3$ | $R^3$-1 (E) | H | T-1 | $CH_3$ | Q-1 | — | CO |

In an embodiment an isoxazoline for use in the invention is as presented in Table 2.

TABLE 2

| $(R^1)_n$ | $R^2$ | $R^3$ | $R^4$ | T | Y | Q | Z | X |
|---|---|---|---|---|---|---|---|---|
| 3-Cl, 5-Cl | $CF_3$ | $CH_2CF_3$ | H | T-2 | — | Q-1 | — | CO |
| 3-Cl, 5-Cl | $CF_3$ | $CH_2CH_3$ | H | T-2 | — | Q-1 | — | CO |
| 3-Cl, 5-Cl | $CF_3$ | $CH_2CH_2OCH_3$ | H | T-2 | — | Q-1 | — | CO |
| 3-Cl, 5-Cl | $CF_3$ | $CH_2C(O)NHCH_2CF_3$ | H | T-2 | — | Q-1 | — | CO |
| 3-$CF_3$, 5-$CF_3$ | $CF_3$ | $CH_2C(O)NHCH_2CF_3$ | H | T-2 | — | Q-1 | — | CO |
| 3-$CF_3$, 5-Cl | $CF_3$ | $CH_2C(O)NHCH_2CF_3$ | H | T-2 | — | Q-1 | — | CO |
| 3-Cl, 5-Cl | $CF_3$ | — | | T-2 | — | Q-6 | $Z^B$-7 | |
| 3-Cl, 5-Cl | $CF_3$ | — | — | T-2 | — | Q-7 | $Z^B$-7 | |
| 3-Cl, 5-Cl | $CF_3$ | — | — | T-2 | — | Q-5 | $Z^B$-7 | |
| 3-Cl, 5-Cl | $CF_3$ | — | — | T-2 | — | Q-2 | $Z^D$-1 | |
| 3-Cl, 5-Cl | $CF_3$ | $CH_2C(O)NHCH_2CF_3$ | H | T-3 | $CH_3$ | Q-1 | — | CO |
| 3-Cl, 5-Cl | $CF_3$ | $CH_2C(O)NHCH_2CC$ | H | T-3 | $CH_3$ | Q-1 | — | CO |
| 3-$CF_3$, 5-$CF_3$ | $CF_3$ | $CH_2C(O)NHCH_2CF_3$ | H | T-3 | $CH_3$ | Q-1 | — | CO |
| 3-Cl, 4-Cl, 5-Cl | $CF_3$ | $CH_2C(O)NHCH_2CF_3$ | H | T-3 | $CH_3$ | Q-1 | — | CO |
| 3-Cl, 4-F, 5-Cl | $CF_3$ | $CH_2C(O)NHCH_2CF_3$ | H | T-3 | $CH_3$ | Q-1 | — | CO |
| 3-Cl, 5-Cl | $CF_3$ | $CH_2C(O)NHCH_2CF_3$ | H | T-20 | — | Q-1 | — | CO |
| 3-$CF_3$, 5-$CF_3$ | $CF_3$ | $CH_2C(O)NHCH_2CF_3$ | $CH_3$ | T-20 | — | Q-1 | — | CO |
| 3-$CF_3$, 5-$CF_3$ | $CF_3$ | $CH_2C(O)NHCH_2CF_3$ | H | T-20 | — | Q-1 | — | CO |
| 3-$CF_3$, 5-$CF_3$ | $CF_3$ | $CH_2C(O)NHCH_2CF_3$ | H | T-21 | — | Q-1 | — | CO |

TABLE 2-continued

| (R¹)ₙ | R² | R³ | R⁴ | T | Y | Q | Z | X |
|---|---|---|---|---|---|---|---|---|
| 3-Cl, 5-Cl | CF₃ | CH₂C(O)NHCH₂CF₃ | H | T-21 | — | Q-1 | — | CO |
| 3-Cl, 5-Cl | CF₃ | CH₂CH₂SCH₃ | H | T-21 | — | Q-1 | — | CO |
| 3-Cl, 4-Cl, 5-Cl | CF₃ | C(O)CH₃ | H | T-22 | F | Q-1 | — | CH₂ |
| 3-Cl, 4-Cl, 5-Cl | CF₃ | C(O)CH(CH₃)₂ | H | T-22 | F | Q-1 | — | CH₂ |
| 3-Cl, 4-Cl, 5-Cl | CF₃ | C(O)-cyclo-propyl | H | T-22 | F | Q-1 | — | CH₂ |
| 3-Cl, 4-F, 5-Cl | CF₃ | C(O)CH₃ | H | T-22 | F | Q-1 | — | CH₂ |
| 3-Cl, 4-Cl, 5-Cl | CF₃ | C(O)CH₂CH₃ | H | T-22 | F | Q-1 | — | CH₂ |
| 3-Cl, 4-F, 5-Cl | CF₃ | C(O)CH₃ | H | T-22 | Cl | Q-1 | — | CH₂ |
| 3-Cl, 5-Cl | CF₃ | CH₂C(O)NHCH₂CF₃ | H | T-1 | CH₃ | Q-1 | — | CO |
| 3-Cl, 5-Cl | CF₃ | R³-1 (Z) | H | T-1 | CH₃ | Q-1 | — | CO |
| 3-Cl, 5-Cl | CF₃ | R³-1 (E) | H | T-1 | CH₃ | Q-1 | — | CO |

In an embodiment an isoxazoline for use in the invention is the compound:

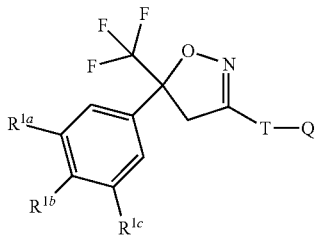

(Formula 2)

wherein $R^{1a}$, $R^{1b}$, $R^{1c}$ are independently from each other: hydrogen, Cl or CF₃.

Preferably $R^{1a}$ and $R^{1c}$ are Cl or CF₃, and $R^{1b}$ is hydrogen, T is

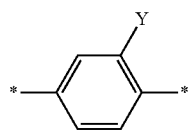

T-1

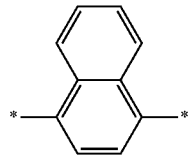

T-2

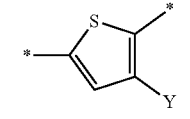

T-3

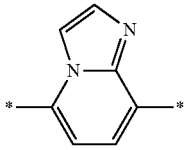

T-20

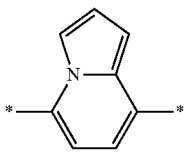

T-21

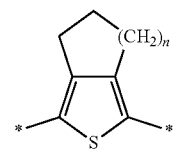

T-23

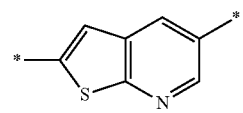

T-24 wherein Y is methyl, bromine, Cl, F, CN or C(S)NH₂; n=1 or 2; and Q is as described above.

In an embodiment of an isoxazoline as defined herein, R³ is H, and R⁴ is: —CH₂—C(O)—NH—CH₂—CF₃, —CH₂—C(O)—NH—CH₂—CH₃, —CH₂—CH₂—CF₃ or —CH₂—CF₃.

The isoxazoline for use in the invention also includes pharmaceutically acceptable salts, esters, and/or N-oxides thereof. In addition, the reference to an isoxazoline compound refers equally to any of its polymorphic forms or stereoisomers.

With respect to stereospecific forms, the pharmaceutical composition according to the invention may employ a racemic mixture of an isoxazoline for use in the invention, containing equal amounts of the enantiomers of such isoxazoline compound as described above. Alternatively, the pharmaceutical composition may use isoxazoline compounds that contain enriched stereoisomers compared to the racemic mixture in one of the enantiomers of the isoxazoline as defined herein. Also, the pharmaceutical composition may use an essentially pure stereoisomer of such isoxazoline compounds. Such enriched- or purified stereoisomer preparations of an isoxazoline for use in the invention, may be prepared by methods known in the art. Examples are chemical processes utilizing catalytic asymmetric synthesis, or the separation of diastereomeric salts (see e.g.: WO 2009/063910, and JP 2011/051977, respectively).

In an embodiment of the pharmaceutical composition according to the invention, the isoxazoline is one or more selected from the group consisting of fluralaner, afoxolaner, lotilaner or sarolaner.

In one embodiment the compound of Formula (I) is 4-[5-(3,5-Dichlorophenyl)-5-trifluoromethyl-4,5-dihydro isoxazol-3-yl]-2-methyl-N-[(2,2,2-trifluoro-ethylcarbamoyl)-methyl]-benzamide (CAS RN 864731-61-3-USAN fluralaner).

In an embodiment, the fluralaner is S-fluralaner.

In another embodiment the compound of Formula (I) is 4-[5-[3-Chloro-5-(trifluoromethyl)phenyl]-4,5-dihydro-5-(trifluoromethyl)-3-isoxazolyl]-N-[2-oxo-2-[(2,2,2-trifluoroethyl)amino]ethyl]-1-naphthalenecarboxamide (CAS RN 1093861-60-9, USAN-afoxolaner) that was disclosed in WO2007/079162.

In an embodiment of the pharmaceutical composition according to the invention the isoxazoline is lotilaner (CAS RN: 1369852-71-0; 3-methyl-N-[2-oxo-2-(2,2,2-trifluoroethylamino)ethyl]-5-[(5S)-5-(3,4,5-trichlorophenyl)-5-(trifluoromethyl)-4H-1,2-oxazol-3-yl]thiophene-2-carboxamide).

In an embodiment of the pharmaceutical composition according to the invention the isoxazoline is sarolaner (CAS RN: 1398609-39-6; 1-(5'-((5S)-5-(3,5-dichloro-4-fluorophenyl)-5-(trifluoromethyl)-4,5-dihydroisoxazol-3-yl)-3'-H-spiro(azetidine-3,1'-(2) benzofuran)-1-yl)-2-(methylsulfonyl) ethanone).

In another embodiment, the compound of Formula (I) is (Z)-4-[5-(3,5-Dichlorophenyl)-5-trifluoromethyl-4,5-dihydroisoxazol-3-yl]-N-[(methoxyimino)methyl]-2-methylbenzamide (CAS RN 928789-76-8).

In another embodiment the compound of Formula (I) is 4-[5-(3,5-dichlorophenyl)-5-(trifluoromethyl)-4H-isoxazol-3-yl]-2-methyl-N-(thietan-3-yl)benzamide (CAS RN 1164267-94-0) that was disclosed in WO2009/0080250.

In an embodiment, the compound according to the invention is 5-[5-(3,5-Dichlorophenyl)-4,5-dihydro-5-(trifluoromethyl)-3-isoxazolyl]-3-methyl-N-[2-oxo-2-[(2,2,2-trifluoroethyl)amino]ethyl]-2-thiophenecarboxamide (CAS RN: 1231754-09-8), which was disclosed in WO 2010/070068.

An embodiment of the invention is a process for preparing isoxazoline compound particles wherein the isoxazoline compound is a compound of Formula (I) comprising
 a) Combining an isoxazoline compound in a crystallizer vessel with a solvent which has a temperature dependent solubility of the isoxazoline compound;
 b) Heating the crystallizer vessel until the isoxazoline compound is dissolved in the solvent;
 c) Cooling the crystallizer vessel to 48-55° C. to form a batch of supersaturated isoxazoline compound in the solvent;
  i) adding crystalline seed of the isoxazoline compound to the crystallizer vessel to initiate crystallization and particle growth;
  ii) Forming a slurry of isoxazoline compound particles and solvent in the crystallizer vessel;
 d) Maintaining the temperature of the crystallizer vessel to 48-55° C.;
 e) Removing a portion of the batch and heating the removed portion to fully dissolve the isoxazoline compound particles in the solvent; wherein the rate of removal is at a rate of approximately 0.25 to 0.75 batch volumes per hour; and wherein the batch volume is the volume of the supersaturated isoxazoline compound solution created in step c);
 f) Returning the dissolved isoxazoline compound solution to the crystallizer vessel; wherein the rate of return is equal to the rate of removal of step e); and
 g) Cooling the crystallizer vessel to achieve isoxazoline compound particles of the desired dimensions;
wherein the desired particle dimensions are particles having a volume weighted particle size distribution (d50) as measured by a light scattering instrument of between 75 and 120 µm and an average particle thickness greater than 10 µm, preferably greater than 20 µm.

In an embodiment, the isoxazoline compound is fluralaner.

In an embodiment, the solvent is methanol or acetone. In yet another embodiment, the solvent is an acetate or acetonitrile. In an embodiment, the solvent is selected from the group of dimethyl acetamide (DMA), N-methylpyrrolidone (NMP), dimethyl sulfoxide (DMSO), N,N-diethy-m-toluamide (DEET), 2-pyrrolidone, acetone, g-hexalactone, glycofurol (tetraglycol), methyl ethyl ketone, diethylene glycol monoethyl ether (Transcutol®), ethyl lactate, dimethylisosorbide, ethyl acetate, macrogol glycerol caprylcaprate (Labrasol®), dipropylene glycol monomethyl ether (Dowanol™ DPM), glycerol formal, benzyl alcohol, methanol, polyethylene glycol 200, propylene carbonate, 1-methoxy-2-propyl acetate (Dowanol™ PMA), isopropylidene glycerol (solketal), ethyl alcohol, glycerol triacetate (triacetin), isopropyl alcohol, propylene glycol, triglycerides medium chain (Miglyol® 812), ethyl oleate, toluene, ethyl acetate or mixtures thereof.

In an embodiment, the solvent is isopropanol.

In an embodiment, the solvent is a mixture of toluene and ethyl acetate.

In an embodiment, the crystallizer of step b is heated to a temperature greater than 60° C., preferably about 65° C.

In an embodiment, in step c) the crystallizer vessel is cooled to achieve supersaturation, preferably to a temperature of about 48-55° C., more preferably to a temperature of about 52-54° C.

In an embodiment, the removed portion is heated to a temperature greater than 60° C., preferably about 65° C.

In an embodiment, the removed portion is heated via a heat exchanger or in a second vessel.

In an embodiment, the rate of removal in step e) is 0.40 to 0.46 batch volumes per hour.

In an embodiment, the rate of removal is maintained for about 4 to 24 hours, preferably about 6 hours.

In an embodiment, the crystallizer vessel of step g) is cooled to a temperature of around 0° C. or less, preferably about −10° C.

An additional embodiment of any of the above processes, further comprising a step of filtering the isoxazoline compound particles of step g).

In an embodiment, the temperature of the filtering is maintained at a temperature of 0° C. or less, preferably at −10° C.

In an embodiment, the filtered isoxazoline particles are dried.

Embodiments of the invention are the isoxazoline compound particles produced by any of processes disclosed herein.

An embodiment of the invention is a isoxazoline compound particle composition comprising particles with a thickness of greater than 10 µm, preferably greater than 20 µm as measured by scanning electron microscopy (SEM), and a mechanical resiliency as measured by a pressure titration using the Sympatec HELOS, wherein the particle size distribution (d50) of the particles does not decrease by more than 40% from 1 to 3 bar dispersion pressure.

In an embodiment, the particle size distribution (d50) of the particles does not decrease by more than 35% from 1 to 3 bar dispersion pressure.

In an embodiment, the particle size distribution (d50) of the particles does not decrease by more than 30% from 1 to 3 bar disp In an embodiment, the isoxazoline compound particle composition comprising particles with a thickness of greater than 10 µm but less than 100 µm, preferably greater than 20 µm but less than 90 µm, preferably greater than 30 µm but less than 80 µm as measured by scanning electron microscopy (SEM).

In an embodiment, the isoxazoline compound particle composition comprising particles with a thickness of greater than 10 µm, preferably greater than 20 µm.

In an embodiment, the isoxazoline compound has a particle size distribution of D50 as measured by a static light scattering instrument of from about 25 microns to about 250 microns, particle size of from about 11 microns to about 250 microns, particle size of from about 50 microns to about 150 microns, particle size of from about 75 microns to about 125 microns, particle size of from about 75 microns to about 150 microns, particle size of from about 90 microns to about 110 microns or a particle size of from about 30 microns to about 100 microns.

Particle size distribution describes the relative amount of particles present according to size. D10 is a particle size distribution that expresses the size that 10% of the particles are smaller than. D50 is a particle size measurement distribution that expresses the size that 50% of the particles are smaller than. D90 is a particle size measurement distribution that expresses the size that 90% of the particles are smaller than.

In a particular embodiment, the D10 of particle size is about 10 µm, about 20 µm, about 30 µm, about 40 µm, about 50 µm, about 60 µm, or about 80 µm.

In a particular embodiment, the D50 of particle size is about 50 µm, about 75 µm, about 80 µm, about 90 µm, about 100 µm, about 110 µm, about 120 µm, about 130 µm about 140 µm or about 150 µm.

In a particular embodiment, the D90 of particle size is about 100 µm, about 130 µm, about 150 µm, about 175 µm, about 200 µm, or about 250 µm.

In a particular embodiment, the D10 of the particle size is about 20 to 35 µm, the D50 of the particle size is about 90 to 105 µm and the D90 of the particle size is about 155 to 175 µm.

In a particular embodiment, the D10 of the particle size is about 25 to 30 µm, the D50 of the particle size is about 95 to 100 µm and the D90 of the particle size is about 160 to 170 µm.

In a particular embodiment, the D10 of the particle size is about 10 to 20 µm, the D50 of the particle size is about 85 to 110 µm and the D90 of the particle size is about 170 to 185 µm.

In a particular embodiment, the D10 of the particle size is about 10 to 15 µm, the D50 of the particle size is about 95 to 105 µm and the D90 of the particle size is about 175 to 180 µm.

In a particular embodiment, the D10 of the particle size is about 10 to 25 µm, the D50 of the particle size is about 40 to 60 µm and the D90 of the particle size is about 95 to 100 µm.

In a particular embodiment, the D10 of the particle size is about 15 to 20 µm, the D50 of the particle size is about 45 to 55 µm and the D90 of the particle size is about 90 to 95 µm.

In a particular embodiment, the D10 of the particle size is about 30 to 50 µm and the D50 of the particle size is about 70 to 130 µm.

In a particular embodiment, the D10 of the particle size is about 35 to 45 µm and the D50 of the particle size is about 90 to 110 µm.

In a particular embodiment, the D10 of the particle size is about 40 µm and the D50 of the particle size is about 100 µm.

The volume weighted particle size can be measured by sieving, microscopy or laser diffraction (Malvern or Sympatec) The volume weighted particle size measurement can be performed with a Malvern Mastersizer 2000 with the Hydro 2000G measuring cell, or with a Horiba LA-910 laser scattering particle size distribution analyzer. The volume weighted particle size can be measured by a Sympatec Helos instrument.

In an embodiment, the isoxazonline compound is fluralaner.

EXAMPLES

Example 1—Process to Form Large Particle Size Fluralaner

Figure 3:
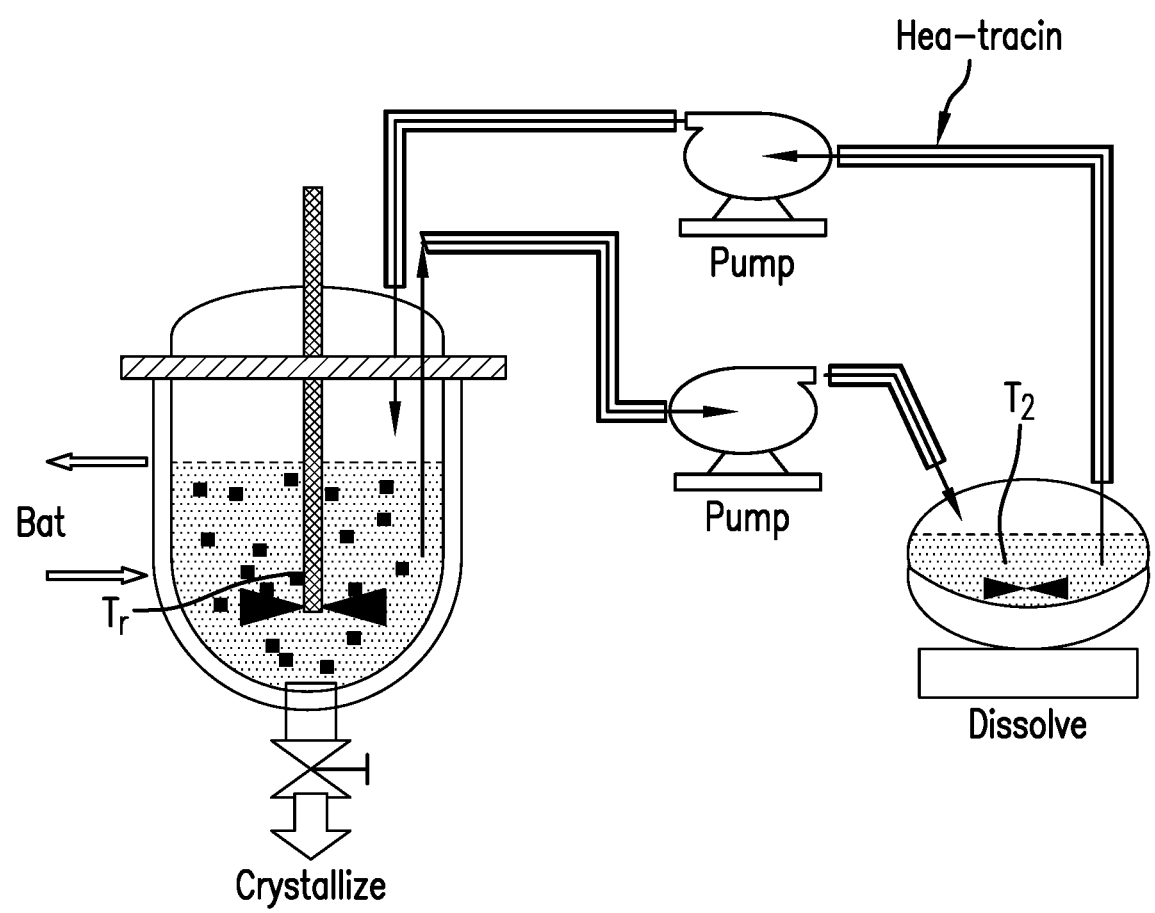
FIG. 3—a schematic diagram of the crystallizer vessel and the other components of the system.

Fluralaner was added at a concentration of 100 mg/mL in IPA, with 60 g added to 600 mL of isopropanol. This composition was heated to 65° C. over 1 hour, and aged for one hour to ensure full dissolution. The solution was cooled over 20 minutes to 50° C. and seeded with 0.6 g of crystalline fluralaner seed. The batch was further cooled to 20° C. over two hours to establish the starting particles. The batch was heated to 54° C., at which point a stream of the batch was removed and heated to an elevated temperature until fully dissolved (>65° C.). The removal rate and return rate to the crystallizer were set to approximately 4.4-4.8 mL/min. The recycle loop continued for 6 hours, at which point the x50 particle size dimension is approximately 40 µm. The batch was aged at 54° C. for 6 hours to further relieve supersaturation, then cooled to 45° C. over 6 hours, and further cooled to 0° C. over 16 hours. See FIG. 3 for a schematic of the process equipment. The resultant slurry was filtered and dried to produce fluralaner particles. The dried fluralaner particles were measured to determine the particle dimensions and mechanical resiliency.

Figure 4A:
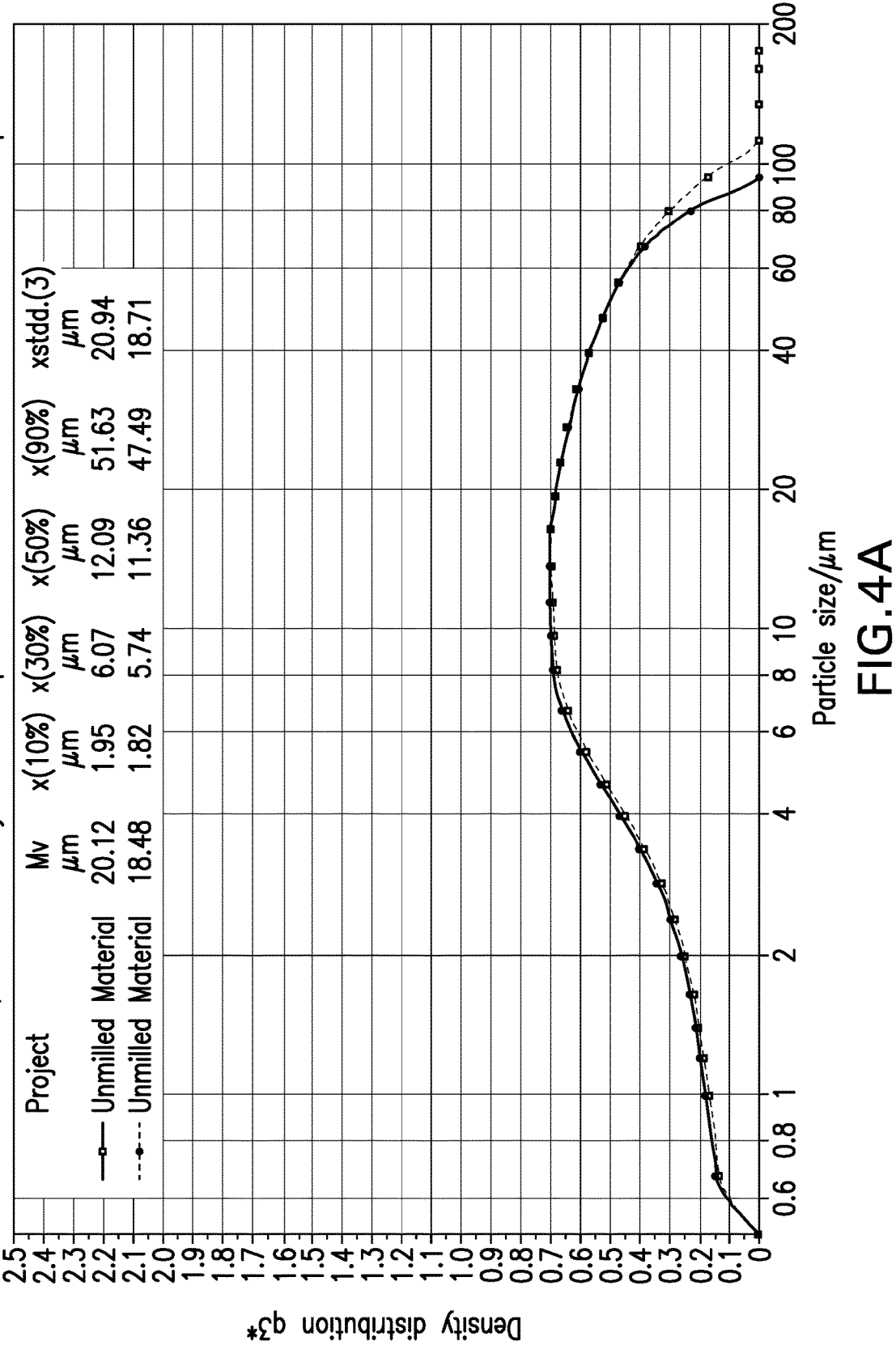
FIG. 4—(3A) Particle size distribution for fluralaner crystals not produced by the inventive process; and (3B) SEM image of the same crystals.
Figure 4B:
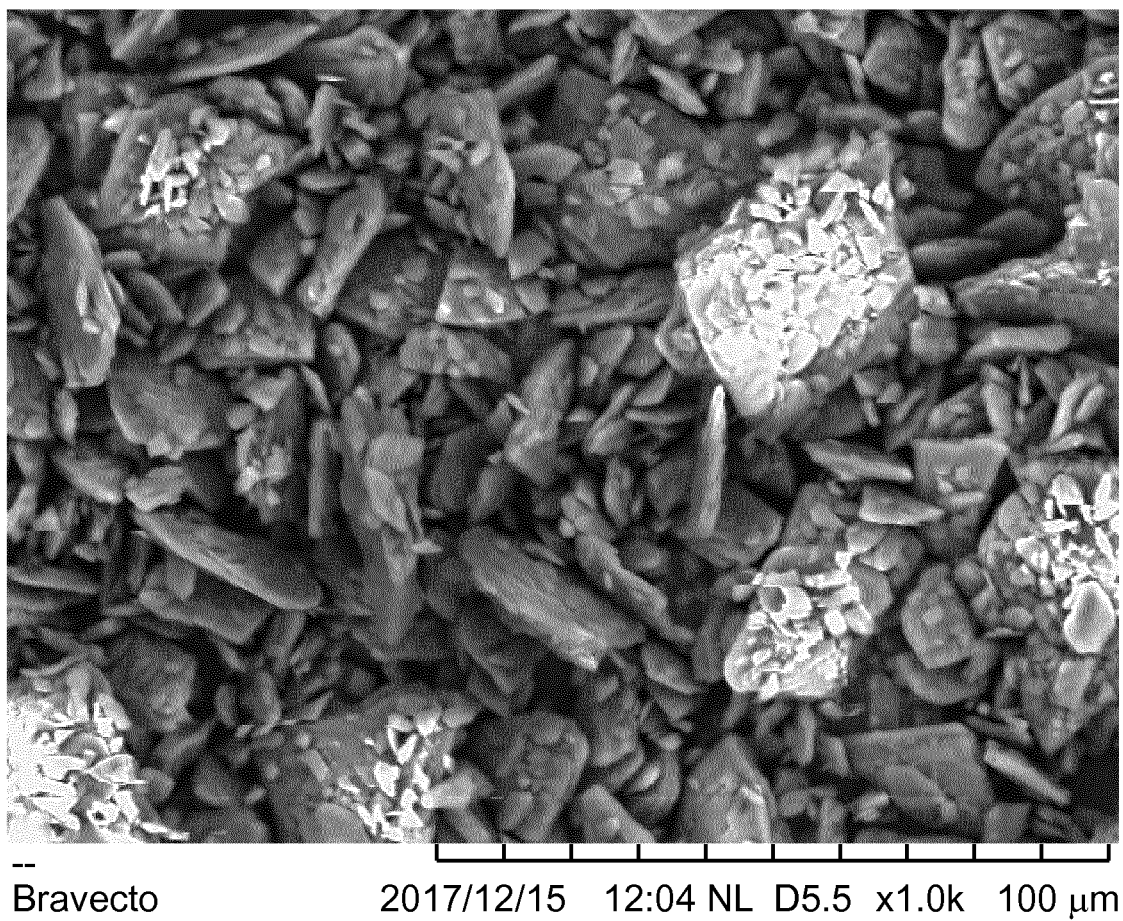
Figure 6:
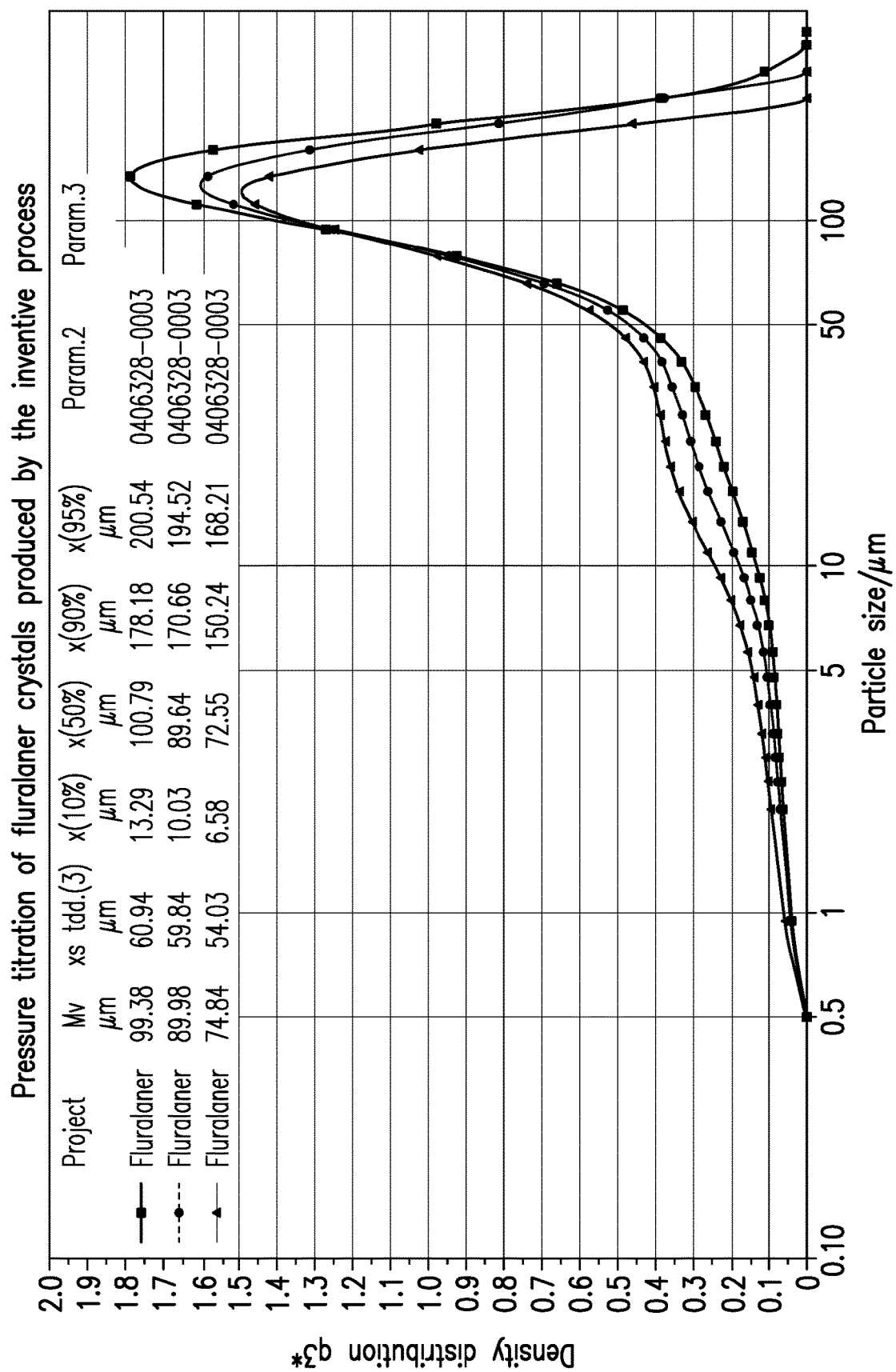
FIG. 6—Particle size distribution and pressure titration of fluralaner crystals produced by the inventive process. Sympatec Pressure Titration: as pressure increased from 1-3 bar, particle size (d50) decreases from 100 um to 73 um.

Example 2—Determination of the Particle Size and Mechanical Resiliency of the Fluralaner Particles The volume weighted particle size of the fluralaner crystals was measured by laser diffraction (Sympatec Helos) to determine the particle size distribution. The mechanical resiliency was also determined during a pressure titration experiment. FIG. 4 shows the particle size distribution fluralaner crystals not produced by the inventive process. In this case, this material is the product of the previous commercial process using an unseeded, distallative crystallization process from an ethyl acetate, toluene solvent system. Of note is the lower particle size and general wider distribution of sizes of the particles.

The fragile nature of particles not representative of the inventive process is demonstrated in FIG. 5, which shows the results of the pressure titration experiment. In this experiment, the particle size distribution was monitored as the particles are exposed to increasing pressure from 1 bar to 3 bar. FIG. 5 shows that as the pressure increased, the median particle size (d50) decreases from 110 µm to 60 µm, a loss of around 45%. Moreover, the particle size distribution curve broadens and shifts towards smaller particle sizes. This is evidence that these particles are being broken under the increased pressure and is an indication that the particles were very thin.

Figure 10:
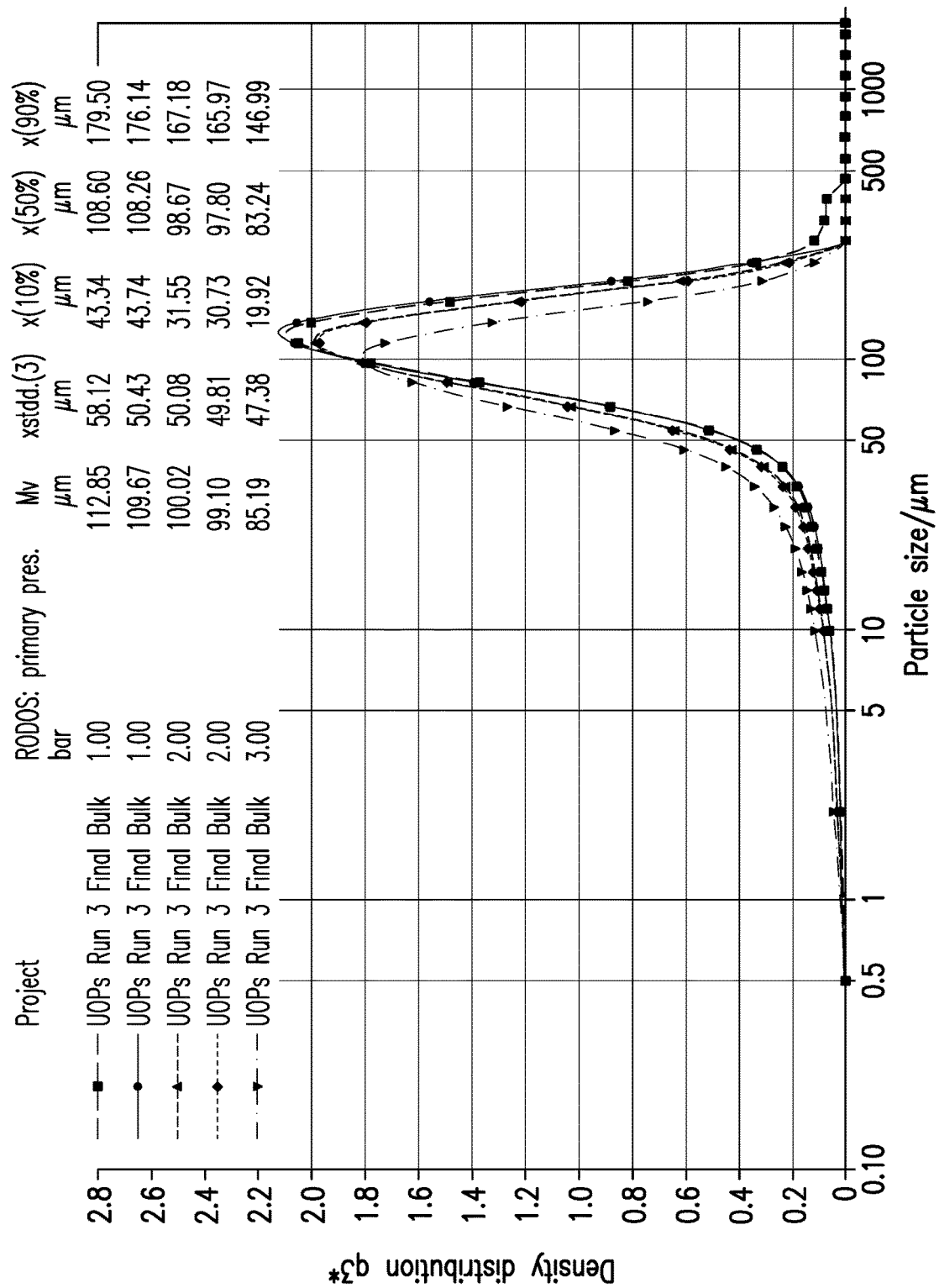
FIG. 10—Particle size distribution of the material made from Example 3. Resulting material had an ×50 of 108, and an approximately 24% reduction in ×50 from the pressure titration from 1 bar to 3 bar.

In contrast, FIG. 10 shows the particle size distribution of the fluralaner crystals produced by the inventive process. These particles have a larger d50 than the particles of FIG. 5. Furthermore, in the pressure titration test, for the particles produced by the inventive process, the d50 was reduced by only around 25% of the original value. This is an indication of the increased mechanical resiliency of these particles. Also of note is the fact that under the elevated pressures, the distribution does not broaden in the same fashion as the particles from the unoptimized process shown in FIG. 5.

Figure 7:
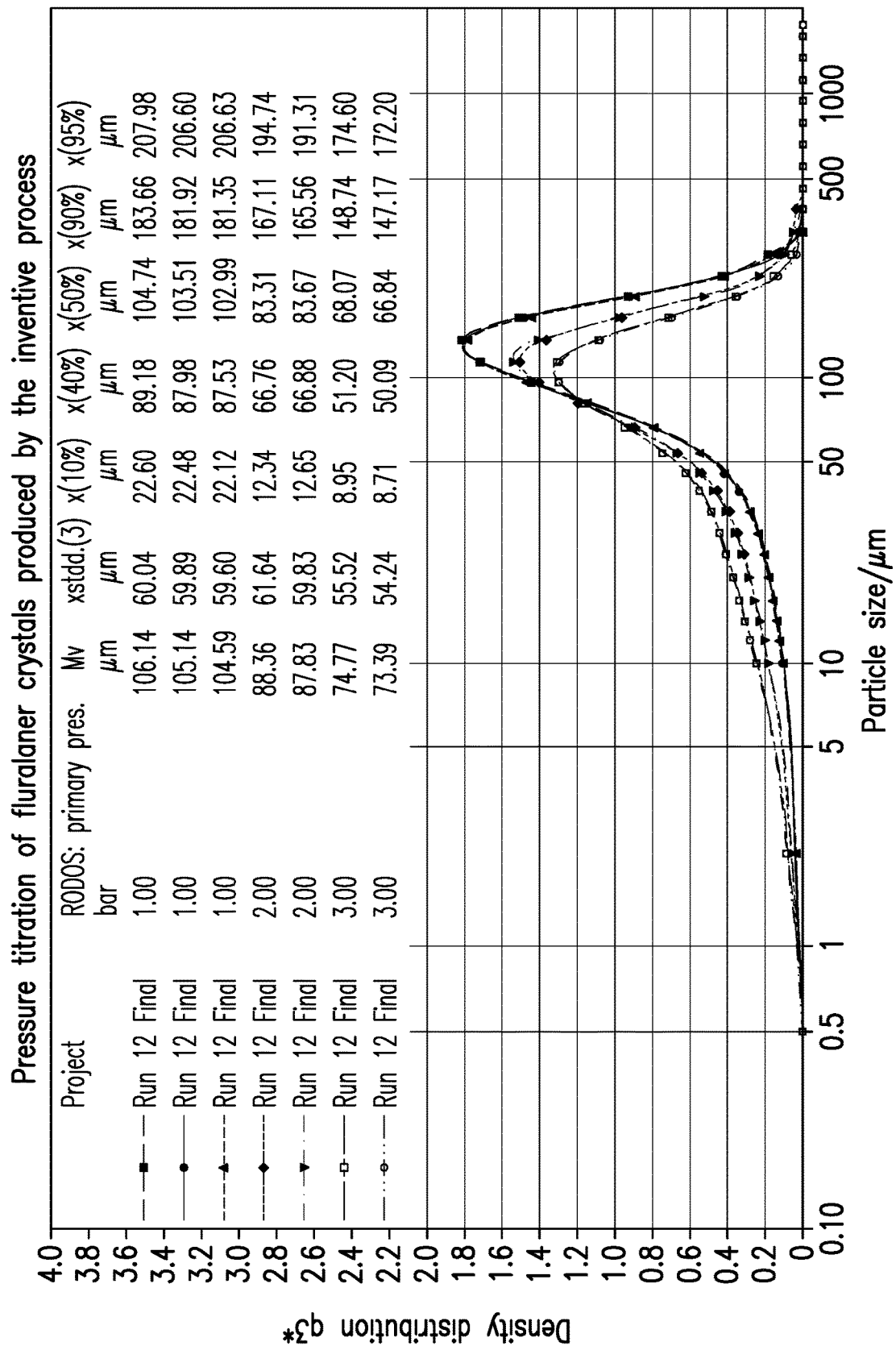
FIG. 7—Particle size distribution and pressure titration of fluralaner crystals produced by the inventive process.

FIG. 7 shows the particle size distribution and pressure titration of an additional batch of fluralaner particles that were produced by the inventive process. In this case, the original d50 of around 103 µm was reduced to around 67 µm, a loss of around 35%.

Figure 8:
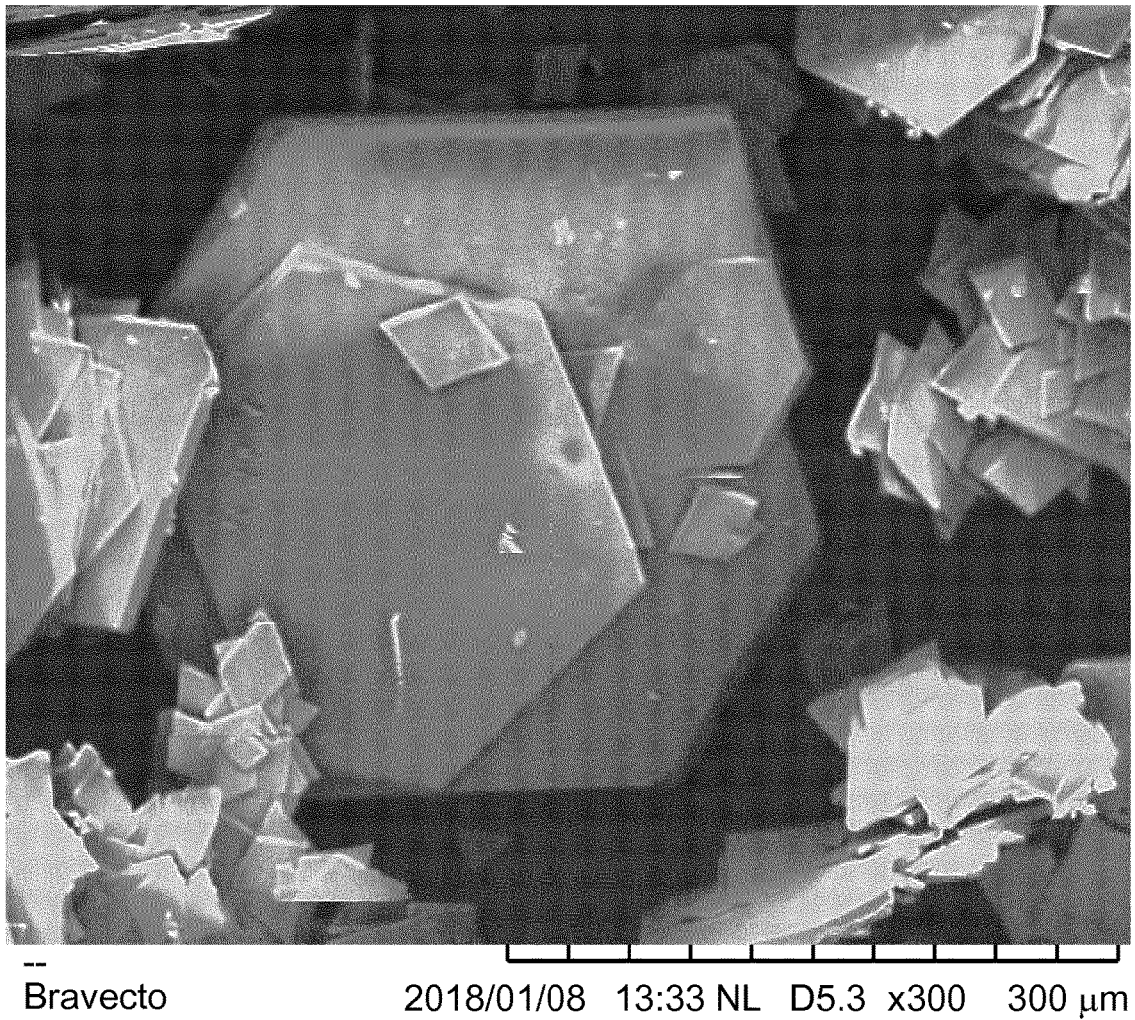
FIG. 8—is a SEM image of fluralaner crystals produced by a process that is not the inventive process.

FIG. 8 is a scanning electron microscopy image of fluralaner particles that were not produced the inventive process. Of note is that these crystals are rather thin.

Figure 9:
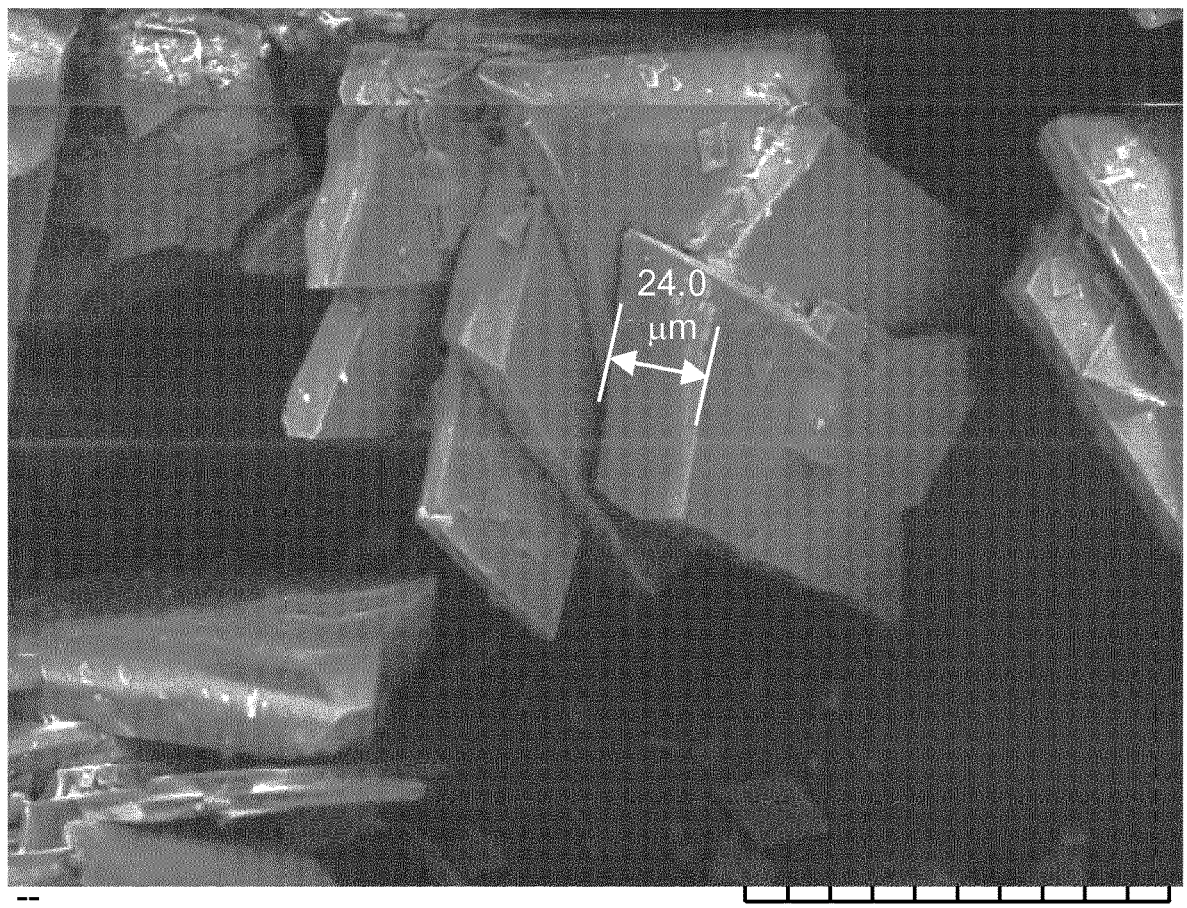
FIG. 9—SEM image of fluralaner crystals produced by the inventive process.

FIG. 9 is a scanning electron microscopy image of fluralaner particles that were produce by the inventive process. In contrast to the particles shown in FIG. 8, these particles are large (around 100 µm) and thick (around 10-20 µm).

Example 3:—Process to Form Large Particle Size Fluralaner at the 6 L Scale

Figure 11:
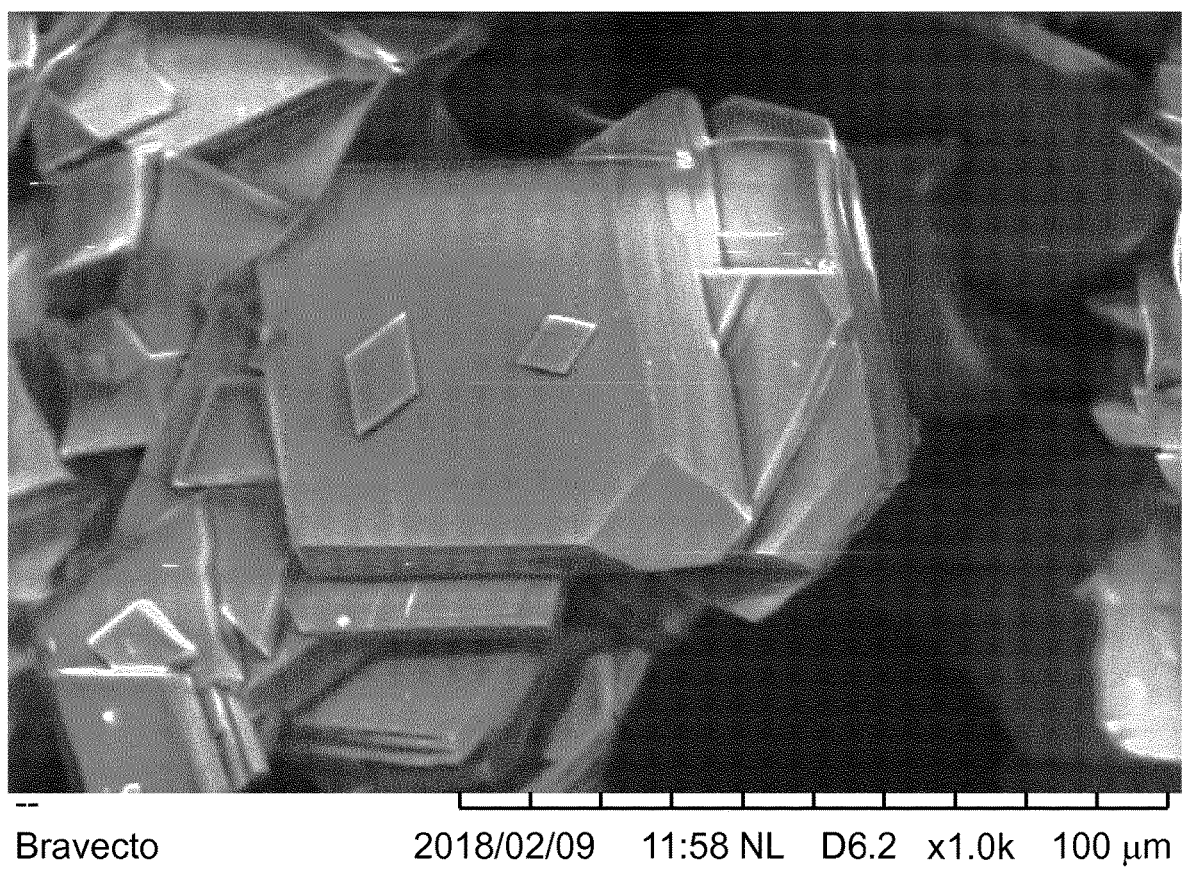
FIG. 11—SEM of the material made from Example 3.

Fluralaner was added at a concentration of 100 mg/mL in isopropanol (IPA), with 600 g added to 6 L of isopropanol. This composition was heated to 65° C. over 1 hour, and aged for one hour to ensure full dissolution. The solution was cooled over 20 minutes to 50° C. and seeded with 6 g of crystalline fluralaner seed, in this instance unmilled seed with an d50 of approximately 10 µm. The batch was further cooled to 20° C. over two hours to establish the starting particles. The batch was heated to 54° C., at which point 1.2 L of the batch was removed and heated to an elevated temperature until all solids were fully dissolved (>65° C.). A recirculation loop was then started, with the removal rate and return rate to the crystallizer set to approximately 44-48 mL/min. The recycle loop continued for 3 hours, at which point the d50 particle size dimension is approximately 45 µm. The batch was aged at 54° C. for 6 hours to further relieve supersaturation, then cooled to 45° C. over 6 hours, and further cooled to 0° C. over 16 hours. The resultant slurry was filtered and dried to produce fluralaner particles. The dried fluralaner particles were measured to determine the particle dimensions and inform mechanical resiliency of the particles, and shown in FIG. 10. See FIG. 11 for an SEM image of the resulting particles.

Example 4:—Process to Form Large Particle Size Fluralaner at the Pilot Scale

Figure 12:
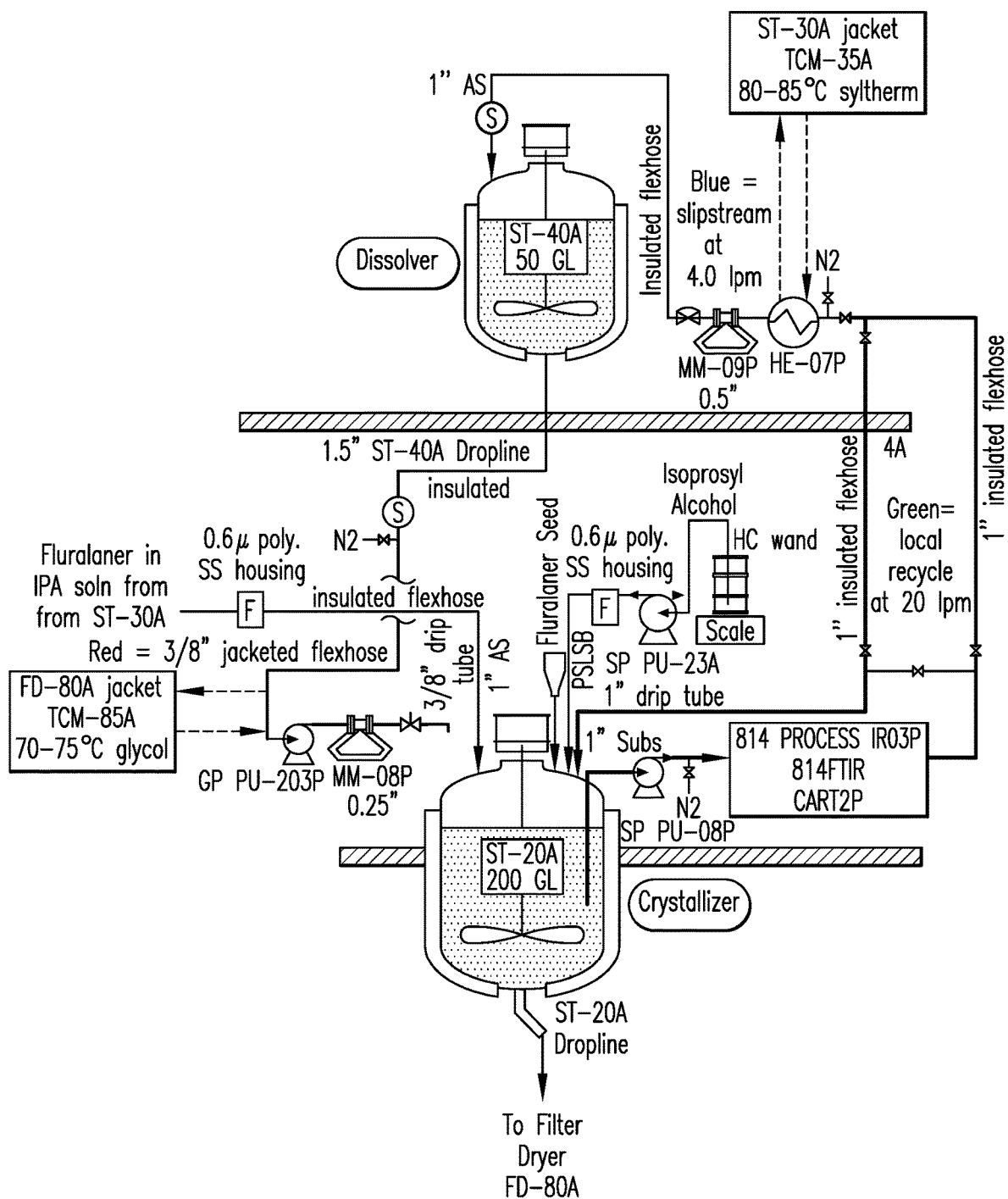
FIG. 12—Schematic of the pilot scale equipment used in Example 4.
Figure 13:
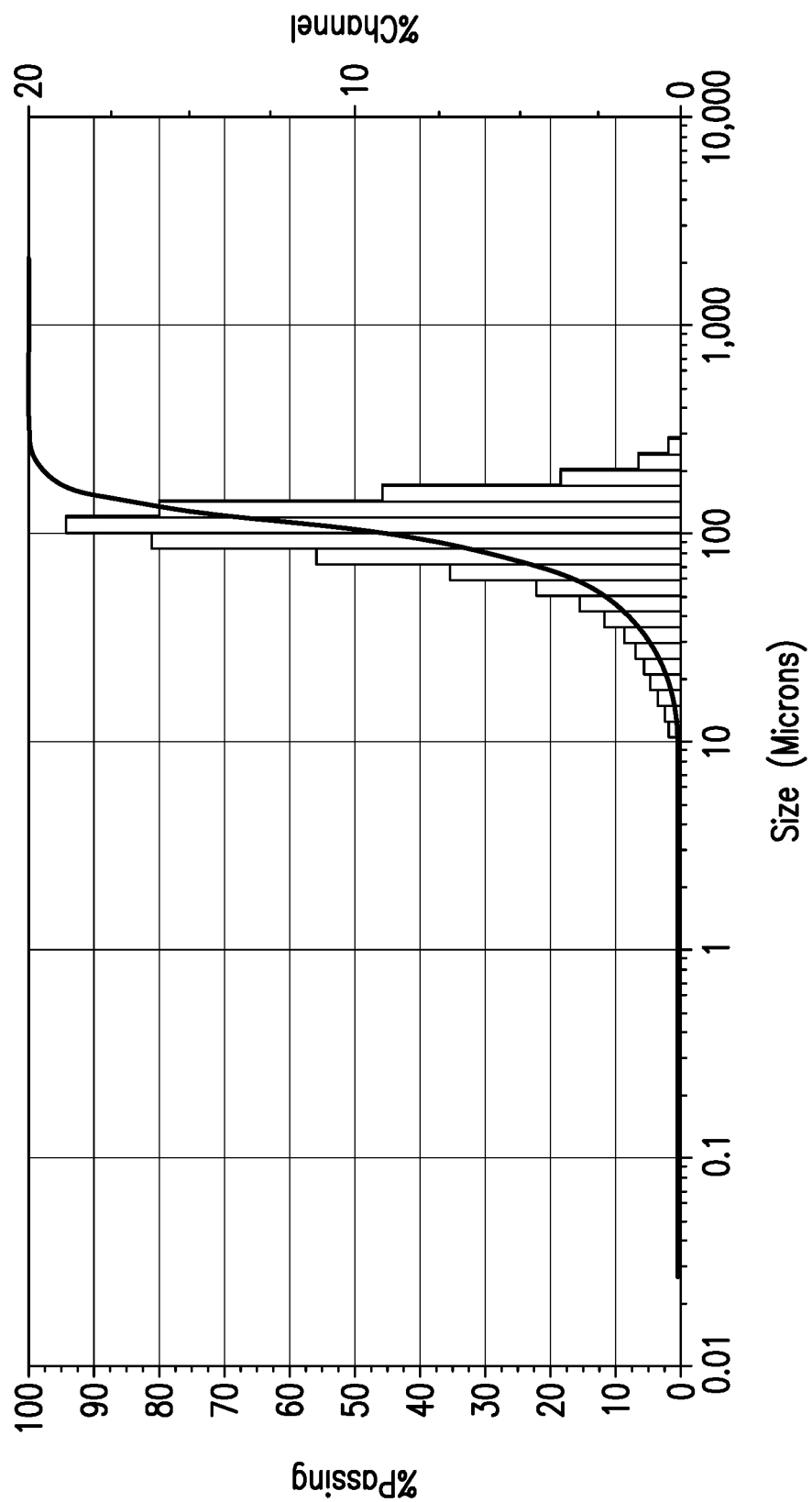
FIG. 13—Particle size distribution of the material made from Example 4. Resulting material had an d50 of 103 μm, and d10 of 47.3 μm and an d90 of 158.8 μm. The particle size measurement for this sample was conducted with a wet method using a Microtrac static light scattering system.
Figure 14:
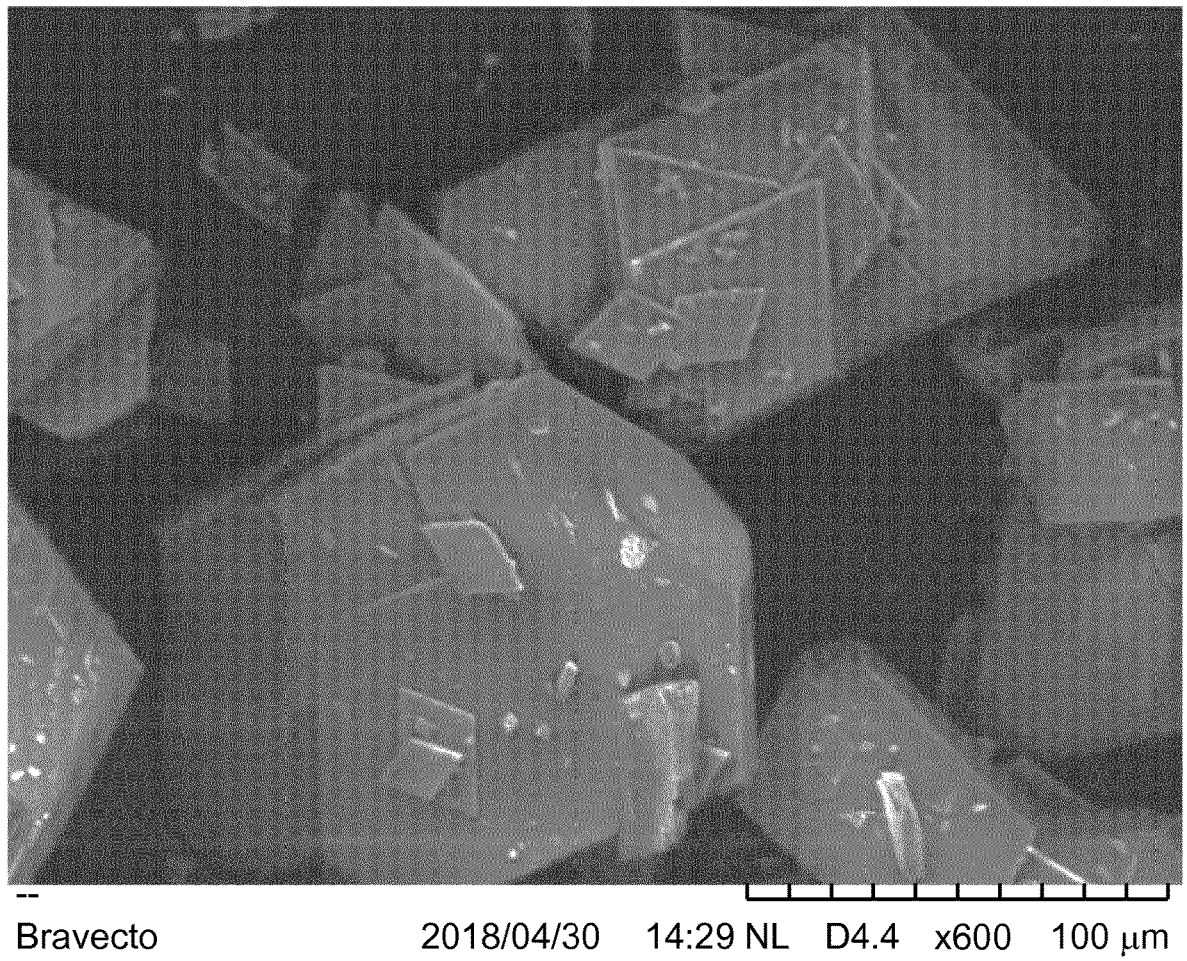
FIG. 14—SEM of the material made from Example 4.

Fluralaner was added at a concentration of 100 mg/mL in IPA, with 60 kg added to 600 L of isopropanol. This composition was heated to 65° C. over 1 hour, and aged for one hour to ensure full dissolution. The solution was cooled over 20 minutes to 50° C. and seeded with 600 g of crystalline fluralaner seed, again with unmilled seed crystals having an d50 of approximately 10 µm. The batch was further cooled to 20° C. over two hours to establish the starting particles. The batch was heated to 54° C., at which point 120 L of the batch was removed and heated to an elevated temperature until fully dissolved (>65° C.). The removal rate and return rate to the crystallizer were set to approximately 4.4-4.8 L/min. The recycle loop continued for 2.75 hours, at which point the d50 particle size dimension is approximately 40 µm. The batch was aged at 54° C. for 6 hours to further relieve supersaturation, then cooled to 45° C. over 6 hours, and further cooled to 0° C. over 16 hours. See FIG. 12 for a schematic of the process equipment. The resultant slurry was filtered and dried to produce fluralaner particles. Agitation was limited during the filtration and drying. The material was delumped at low speed in a conical mill. The dried fluralaner particles were measured to determine the particle dimensions and mechanical resiliency. See FIG. 13 for the particle size distribution and mechanical resiliency. See FIG. 14 for an SEM image of the resulting particles.

Figure 15:
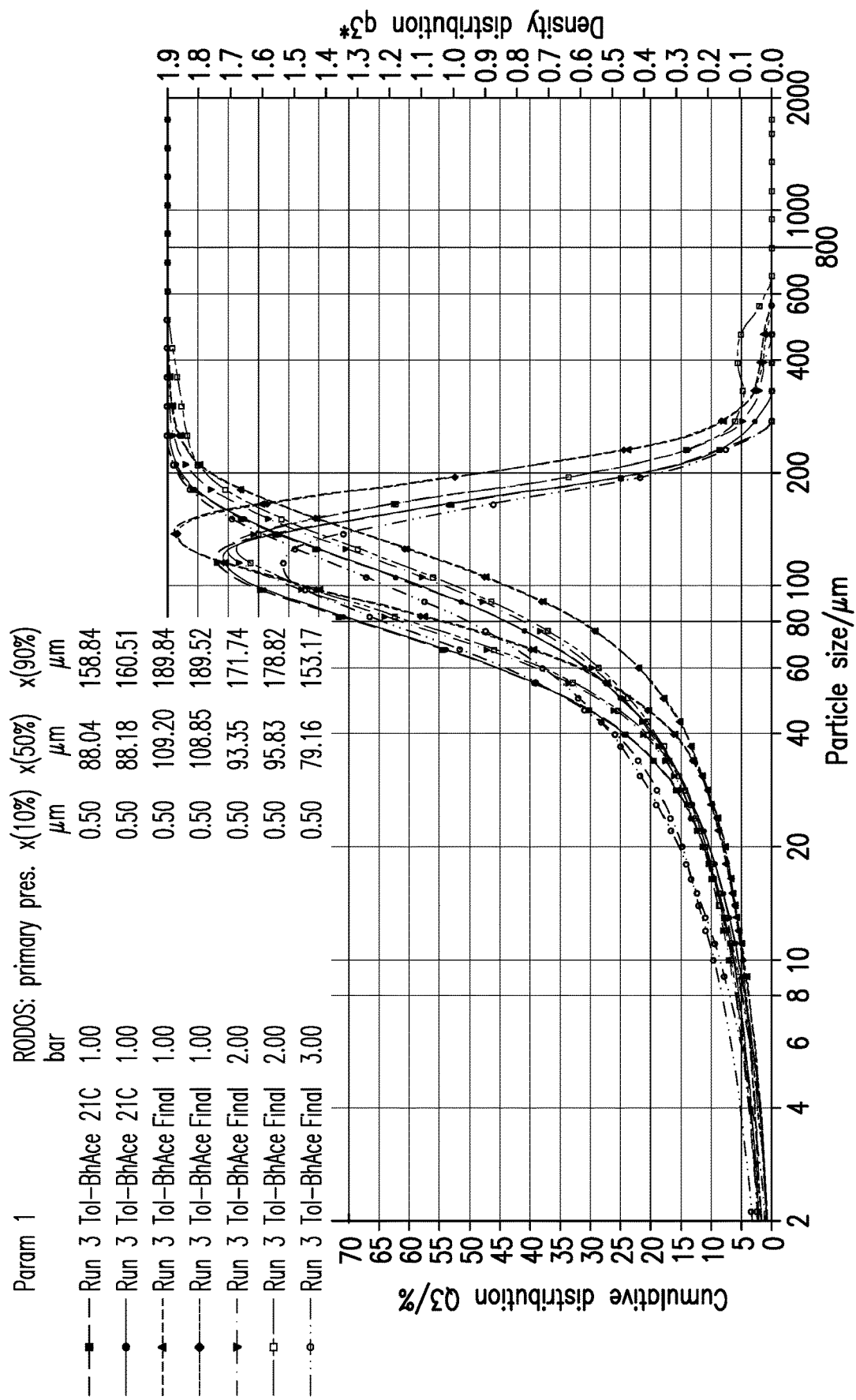
FIG. 15—Particle size distribution of the material made from Example 5. Resulting material had an average d50 of 99 μm, and an approximately 20% reduction in d50 from the pressure titration from 1 bar to 3 bar.
Figure 16:
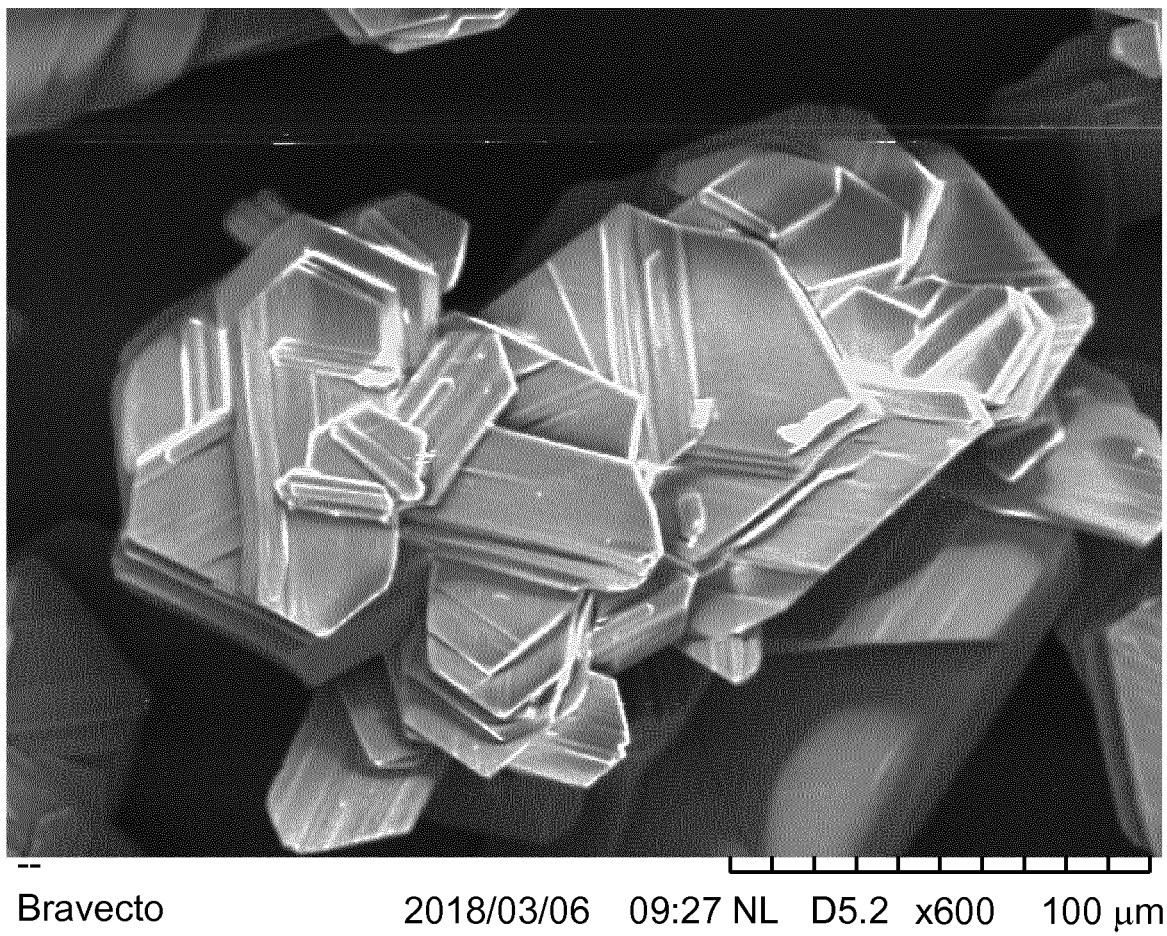
FIG. 16—SEM of the material made from Example 5.

Example 5:—Process to Form Large Particle Size Fluralaner from an Alternative Solvent System Fluralaner was added at a concentration of 100 mg/mL in 5:3 (volume basis) of Toluene:Ethyl Acetate, with 60 g added to 600 mL of solvent. This composition was heated to 65° C. over 1 hour, and aged for one hour to ensure full dissolution. The solution was cooled over 20 minutes to 50° C. and seeded with 0.6 g of crystalline fluralaner seed, again with unmilled seed crystals having an d50 of approximately 10 µm. The batch was further cooled to 20° C. over two hours to establish the starting particles. The batch was heated to 54° C., at which point 120 mL of the batch was removed and heated to an elevated temperature until fully dissolved (>65° C.). The removal rate and return rate to the crystallizer were set to approximately 4.3 mL/min. The recycle loop continued for 2.2 hours, at which point the ×50 particle size dimension is approximately 50 µm. The batch was aged at 54° C. for 5 hours to further relieve supersaturation, then cooled to 45° C. over 6 hours, and further cooled to 0° C. over 16 hours. The dried fluralaner particles were measured to determine the particle dimensions and mechanical resiliency. See FIG. 15 for the particle size distribution and mechanical resiliency as measured with the pressure titration on the Sympatec static light scattering system. See FIG. 16 for an SEM image of the resulting particles. These results show that using the recirculation process, the target particle size and mechanical resiliency can be achieved. It should be noted that the solvent may impact the morphology, as is observed in FIG. 16, where the surfaces of the crystals are slightly modified from the surfaces of crystals grown from isopropanol.

The invention claimed is:

1. An isoxazoline compound particle composition comprising particles having a volume weighted particle size distribution (d50) as measured by a static light scattering instrument of between 50 and 150 µm and with a thickness of greater than 10 µm, as measured by scanning electron microscopy (SEM) wherein, the volume weighted particle size distribution (d50) as measured by a static light scattering instrument of the particles does not decrease by more than 40% when the mechanical resiliency as measured by a pressure titration is increased from 1 to 3 bar dispersion pressure, wherein the isoxazoline compound is fluralaner.

2. The isoxazoline compound particle composition of claim 1 wherein the particle size distribution (d50) of the particles does not decrease by more than 35% from 1 to 3 bar dispersion pressure.

3. The isoxazoline compound particle composition of claim 1, wherein the volume weighted particle size distribution (d50) as measured by a static light scattering instrument is between 75 and 120 µm.

4. The isoxazoline compound particle composition of claim 1, wherein the thickness is greater than 20 μm as measured by scanning electron microscopy (SEM).

* * * * *